(12) United States Patent
Rowell et al.

(10) Patent No.: US 7,923,682 B2
(45) Date of Patent: Apr. 12, 2011

(54) FINGERPRINT ANALYSIS USING MASS SPECTROMETRY

(75) Inventors: Frederick John Rowell, Durham (GB); Brendan John Theaker, Tees Valley (GB)

(73) Assignee: University of Sunderland (GB)

( * ) Notice: Subject to any disclaimer, the term of this patent is extended or adjusted under 35 U.S.C. 154(b) by 639 days.

(21) Appl. No.: 11/501,053

(22) Filed: Aug. 9, 2006

(65) Prior Publication Data

US 2007/0187587 A1 Aug. 16, 2007

Related U.S. Application Data

(60) Provisional application No. 60/831,204, filed on Jul. 17, 2006, provisional application No. 60/795,599, filed on Apr. 28, 2006, provisional application No. 60/706,439, filed on Aug. 9, 2005, provisional application No. 60/706,438, filed on Aug. 9, 2005.

(30) Foreign Application Priority Data

| Aug. 9, 2005 | (GB) | .................................. 0516271.4 |
| Aug. 9, 2005 | (GB) | .................................. 0516272.2 |
| Apr. 28, 2006 | (GB) | .................................. 0608464.4 |
| May 26, 2006 | (GB) | .................................. 0610453.3 |

(51) Int. Cl.
*H01J 49/04* (2006.01)
(52) U.S. Cl. ...................................... 250/287
(58) Field of Classification Search .................. 250/287, 250/282; 436/86, 161, 173, 175; 435/7.31, 435/7.32; 800/301, 279
See application file for complete search history.

(56) References Cited

U.S. PATENT DOCUMENTS

| 3,075,852 | A | 1/1963 | Bonora |
| 4,176,205 | A | 11/1979 | Molina |
| 4,837,260 | A | 6/1989 | Sato et al. |
| 5,204,088 | A | 4/1993 | Noebel et al. |
| 6,048,546 | A | 4/2000 | Sasaki et al. |
| 6,194,213 | B1 | 2/2001 | Barbera-Guillem |
| 6,299,674 | B1 | 10/2001 | Takamura et al. |
| 6,306,662 | B1 | 10/2001 | Menzel |
| 6,495,352 | B1 | 12/2002 | Brinker et al. |
| 6,720,564 | B1 | 4/2004 | Koch |
| 6,743,558 | B2 | 6/2004 | Yamaguchi et al. |
| 6,905,879 | B2 * | 6/2005 | Qiu et al. ........................ 436/86 |
| 7,071,386 | B2 * | 7/2006 | Bintrim et al. ................ 800/301 |
| 7,258,874 | B2 | 8/2007 | Barbe et al. |
| 2002/0001716 | A1 | 1/2002 | Barbera-Guillem |
| 2002/0055051 | A1 | 5/2002 | Kudo et al. |

(Continued)

FOREIGN PATENT DOCUMENTS

EP 1369907 A2 12/2003

(Continued)

OTHER PUBLICATIONS

International Search Report for PCT/GB2006/050234.

(Continued)

*Primary Examiner* — Kiet T Nguyen
(74) *Attorney, Agent, or Firm* — Katten Muchin Rosenman LLP

(57) ABSTRACT

The present invention is directed to a method for determining the presence of a residue on or within a fingerprint using matrix-assisted mass spectrometric techniques. The matrix-assisted mass spectrometric technique can be selected from Matrix-Assisted Laser Desorption/Ionization Mass Spectrometry Time-Of-Flight Mass Spectrometry (MALDI-TOF-MS) and/or Surface Assisted Laser Desorption/Ionisation Time-Of-Flight Mass Spectrometry (SALDI-TOF-MS).

32 Claims, 15 Drawing Sheets

U.S. PATENT DOCUMENTS

2004/0185513 A1* 9/2004 Demirev ............ 435/7.31

FOREIGN PATENT DOCUMENTS

| WO | 01/62232 A1 | 8/2001 |
| --- | --- | --- |
| WO | 03/083481 A2 | 10/2003 |
| WO | 2004/063387 A2 | 7/2004 |
| WO | 2005/066632 A1 | 7/2005 |

OTHER PUBLICATIONS

Written Opinion of the International Searching Authority for PCT/GB2006/050234.
J. Wei, et al., "Desorption-ionization mass spectrometry on porous silicon", Nature, vol. 399, May 20, 1999, pp. 243-246, (XP002133206).
A. Crecelius, et al., "Thin-layer chromatography-matrix-assisted laser desorption ionisation-time-of-flight mass spectrometry using particle suspension matrices", Journal of Chromatography A, vol. 958, No. 1-2, Jun. 7, 2002, pp. 249-260, (XP004358056).
J. S. Day, et al., "The detection of drugs of abuse in fingerprints using Raman spectroscopy. I. Latent fingerprints", Spectrochimica Acta A (Molecular and Biomolecular Spectroscopy), vol. 60A, No. 3, Feb. 2004, pp. 563-568, (XP002408051).
M. V. Buchanan, et al., "Chemical characterisation of fingerprints from adults and children", Proceedings of the SPIE—The International Society for Optical Engineering, vol. 2941, 1997, pp. 89-95, (XP002408052).
I. Cotte-Rodríguez, et al., "Desorption Electrospray Ionization of Explosives on Surfaces: Sensitivity and Selectivity Enhancement by Reactive Desorption Electrospray Ionization", Analytical Chemistry, vol. 77, No. 21, Nov. 1, 2005, pp. 6755-6764, (XP002408053).
N. E. Archer, et al., "Changes in the lipid composition of latent fingerprint residue with time after deposition on a surface", Forensic Science International, 154, (2005), pp. 224-239.
J. Cao, et al., "Preparation and radiolabeling of surface-modified magnetic nanoparticles with rhenium-188 for magnetic targeted radiotherapy", Journal of Magnetism and Magnetic Materials, 277, (2004), pp. 165-174.
J. S. Day, et al., "The detection of drugs of abuse in fingerprints using Raman spectroscopy II: cyanoacrylate-fumed fingerprints", Spectrochimica Acta Part A, 60, (2004), pp. 1725-1730.
M. A. Huestis, et al., "Sweat testing for cocaine, codeine and metabolites by gas chromatography—mass spectrometry", Journal of Chromatography B, 733, (1999), pp. 247-264.
D. A. Kidwell, et al., "Testing for drugs of abuse in saliva and sweat", Journal of Chromatography B, 713, (1998), pp. 111-135.
Examination Report for EP 06765382 mailed May 14, 2009 (6 pages).
K. L. Busch, et al., "Desorption Ionization Mass Spectrometry", Journal of Mass Spectrometry, 30, (1995), pp. 233-240.
International Search Report for International Application PCT/GB2005/000038 with a mailing date of Jun. 13, 2005.
Balachandran et al., Advances in Cryogenic Engineering (The Effect of Nanostructure on the Thermal Behavior of Aerogels), 2000, Kluwer Academic/Plenum; vol. 46, pp. 345-349.
Champod et al., Fingerprints and Other Ridge Skin Impressions, CRC Press, Boca Raton, (2004), (Ch. 4, Appxs 3 & 4).
Expert Group on Vitamins and Minerals Secretariat, "Review of Silican", Aug. 2002.
Harris et al., "Magnetite Nanoparticle Dispersions Stabilized by Triblock Copolymers", Chemistry of Materials, 15, (2003), p. 1367.
International Search Report and Written Opinion for PCT/GB2006/050233 mailed Jan. 17, 2007 (17 pages).
Krause, E., Wenschuh H. et al. "The dominance of arginine-containing peptides in Maldi-derived tryptic mass fingerprints of proteins". Anal Chem. Oct. 1, 1999; 71 (19): 4160-5.
Menzel et al., "Functionalized Europium Oxide Nanoparticles for Fingerprint Detection—A Preliminary Study", J. Forensic (dent., vol. 55, Issue 2, Mar./Apr. 2005, pp. 189 to 195.
Menzel et al., "Photoluminescent CdS/Dendrimer Nanocomposites for Fingerprint Detection", Journal of Forensic Sciences, (2000), pp. 770-773.
Menzel et al., "Photoluminescent Semiconductor Nanocrystals for Fingerprint Detection", Journal of Forensic Sciences, (1999), pp. 545-551.
Miller et al., Aerogel Fingerprint Media; Sep. 1999; Office of Scientific and Technical Information (OSTI); pp. 1-21.
Rao et al., "Synthesis and Characterization of Hydrophobic Silica Aerogels Using Trimethylethoxysilane as a Co-Precursor", Journal of Sol-Gel Science and Technology, vol. 27, 2003, pp. 103-109.
Sakka, Handbook of Sol-Gel Science and Technology: Processing Characterization and Applications, Nov. 2004, Springer, 1 edition, pp. 34-35.
Sodhi et al., "Powder Method for Detecting Latent Fingerprints: A Review", Forensic Sci. Int., 120, (2001), pp. 172-176.
Suckau D., Resemann A. et al. A novel MALDI LIFT-TOF/TOF mass spectrometer for proteomics. Anal Bioanal Chem., Aug. 2003; 376 (7): 952-65.
Tapec et al, Development of Organic Dye-Doped Silica Nanoparticles for Bioanalysis and Biosensors, J. Nanosci. Nanotech. 2002, 2(3-4), 405-409.
Wagh, "Chemically Bonded Phosphate Ceramics: Twenty-First Century Materials with Diverse Applications", Jan. 2005, Elsevier Science, p. 135.

* cited by examiner

| Rh. 6G FP | Rh 6G + TiO$_2$/PTEOS | Residual on Glass Slide | Lifted Tape and Prints |
|---|---|---|---|
| Fig 1a | Fig. 1b | Fig 1c | Fig 1d |

Figure 10;
10a)
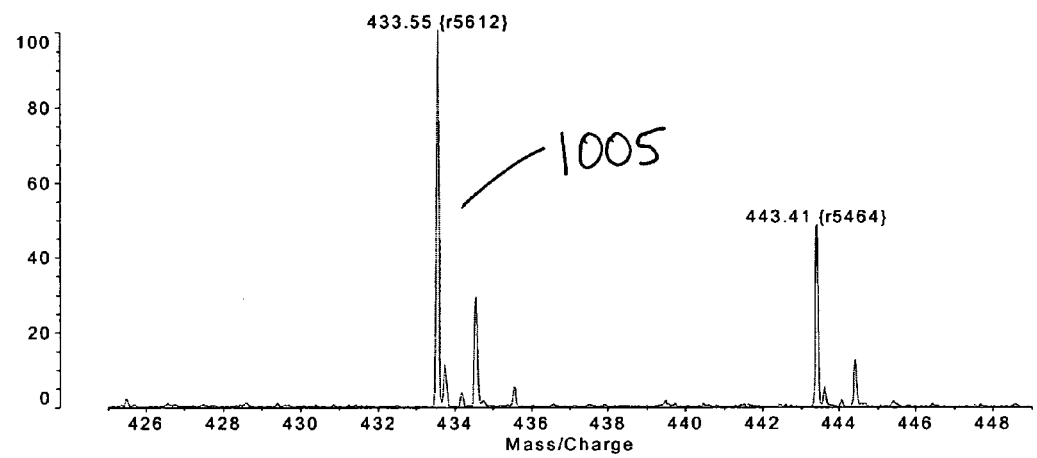
10b)
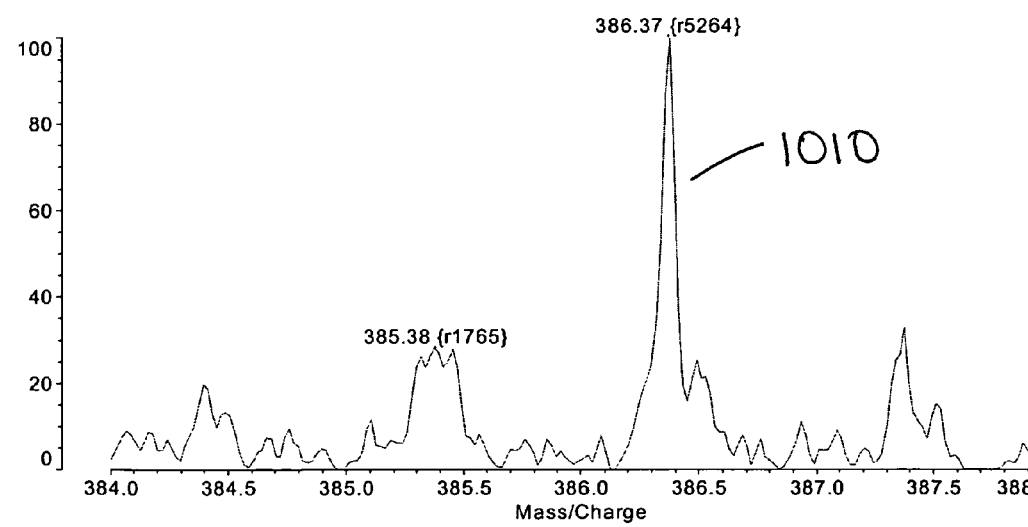

FINGERPRINT ANALYSIS USING MASS SPECTROMETRY

This application claims priority under 35 U.S.C. §119(e) to U.S. Provisional Application No. 60/706,439, filed on Aug. 9, 2005, U.S. Provisional Application No. 60/706,438, filed on Aug. 9, 2005, U.S. Provisional Application No. 60/795,599, filed on Apr. 28, 2006, and U.S. Provisional Application No. 60/831,204, filed on Jul. 17, 2006, the entire contents of each of which are hereby incorporated by reference herein. This application also claims priority under 35 U.S.C. §119 to Great Britain Patent Application No. 0514272.2, filed on Aug. 9, 2005, Great Britain Patent Application No. 0516271.4, filed on Aug. 9, 2005, Great Britain Patent Application No. 0608464.4, filed on Apr. 28, 2006, and Great Britain Patent Application No. 0610453.3, filed on May 26, 2006, the entire contents of each of which are hereby incorporated by reference herein.

BACKGROUND

1. Field of the Invention

The present invention relates to a method for determining the presence of a residue within a fingerprint using mass spectrometric techniques.

2. Background Information

Latent fingerprints contain numerous compounds, such as naturally occurring compounds from the body, e.g., cholesterol, squalene and fatty acids, or compounds which may be left on the latent fingerprint from a contact, e.g., cocaine or other drugs of abuse, as discussed in, for example: R. S. Ramotowski, in: H. C. Lee and R. E. Gaensslen (Eds.) *Advances in Fingerprint Technology* (2nd Ed.), CRC Press, Boca Raton, Fla., 2001, page 63 (hereinafter, the "Ramotowski reference"); K. G. Asano, C. K. Bayne, K. M. Horsman and M. V. Buchanan, J. Forensic Sci., 47, (2002), pages 1-3 (hereinafter, the "Asano reference"); and N. E. Archer, Y. Charles, J. A. Elliott. and S. Jickells, "Changes in the lipid concentration of latent fingerprint residue with time after deposition on a surface." Forensic Sci. Int. (Article in Press) (hereinafter, the "Archer reference"). Of the studies to date with this objective, use has been made of Raman spectroscopy, as discussed in, for example: J. S. Day, H. G. M. Edwards, S. A. Dobrowski and A. M. Voice, "The detection of Drugs of Abuse in Fingerprints using Raman Spectroscopy I: Latent Fingerprints," Spectrochimica Acta A, 60 (2004), page 563 (hereinafter, the "first Day reference"); and J. S. Day, H. G. M. Edwards, S. A. Dobrowski and A. M. Voice, "The detection of Drugs of Abuse in Fingerprints using Raman Spectroscopy I: Cyanoacrylate-Fumed Fingerprints," Spectrochimica Acta A, 60 (2004), page 1725 (hereinafter, the "second Day reference").

In these studies, difficulty was observed in visually locating the drugs of abuse in order to perform the analysis and the method was also relatively insensitive and relatively non-specific. The most common method for the interrogation of latent fingerprints is Gas Chromatography-Mass Spectrometry (GC-MS). It has previously been shown that residues from latent fingerprints can be extracted into a solvent and analyzed by GC-MS, as discussed in, for example, the Asano and Archer references. Such compounds include squalene and cholesterol, however, levels of these on latent fingerprints vary, not only between individuals, but between times for the same individual, as discussed in, for example, the Archer reference. GC-MS has also been used to detect contact residues, such as cocaine from spiked fingerprints, with a limit of detection of approx 300 µg (as described in, for example, J. P. Nielson and A. I. Katz, "A Processing Protocol for Drug Residue and Latent Print Evidence," J. Forensic Sci., 33 (1998), pages 1463-1472 (hereinafter, the "Nielson reference")) and for the detection of drugs of abuse and metabolites from commercial sweat patches down to ng per patch levels (as described in, for example, M. A. Heustis, J. M. Oyler, E. J. Cone, A. T. Wstadik, D. Schoendorfer and R. E. Joseph, "Sweat Testing for Cocaine, Codeine and Metabolites by Gas Chromatoraphy-Mass Spectrometry," J. Chromatogr. B. 733 (1999), page 247 (hereinafter, the "Heustis reference")) and from saliva (as described in, for example, D. A. Kidwell, J. C. Holland and S. Athanaselis, "Testing for Drugs of Abuse in Saliva and Sweat," J. Chromatogr. B. 713 (1998), page 111 (hereinafter, the "Kidwell reference")). However, all of the above-mentioned methods require complicated extraction procedures to be undertaken prior to analysis.

Matrix-Assisted Laser Desorption/Ionization Mass Spectrometry Time-Of-Flight Mass Spectrometry (MALDI-TOF-MS) was developed in late 1980s by Karas and Hillenkamp, and has become established as a technique for the analysis and accurate molecular weight determination of large macromolecules such as proteins, polysaccharides, nucleic acids and synthetic polymers with high mass accuracy and extreme sensitivity. MALDI is a "soft" ionization process that produces minimum fragmentation, and in which the energy from the laser is spent in volatilizing the matrix rather than in degrading the macromolecule. MALDI-TOF-MS has not been considered in the field of identifying residues present on latent fingerprints. MALDI-TOF-MS is termed Surface Assisted Laser Desorption/Ionization (SALDI) when graphite, titanium dioxide or silica are used as suspension matrices for MALDI, as described in, for example: J. Sunner, E. Dratz and Y. C. Chen, "Graphite Surface-Assisted Laser Desorption/Ionization Time-of-Flight Mass Spectrometry of Peptides and Proteins from Liquid Solutions," Anal. Chem. 67 (1995), page 4335 (hereinafter, the "Sunner reference"); and A. Crecelius, M. R. Clench, D. S. Richards and V. Parr, "Thin-Layer Chromatography-Matrix-Assisted Laser Desorption Ionisation-Time-of-Flight Mass Spectrometry Using Particle Suspension Matrices," J. Chromatogr. A. 958 (2002), page 249 (hereinafter, the "Crecelius reference").

SUMMARY OF THE INVENTION

The present invention discloses various materials that can be used in detection and/or imaging of fingerprints. These materials are also capable of acting as matrix-agents in various mass spectrometric techniques. Thus, these materials have particular properties enabling them to carry out such a "dual-purpose" role.

Thus, in one aspect of the present invention, there is provided a method of determining the presence of a residue in a fingerprint, the method comprising the steps of:
  i) applying to the fingerprint a particulate matter comprising a material which (1) is capable of acting as a matrix agent or material in a matrix-assisted mass spectrometric technique; and (2) aids detection and/or imaging of a fingerprint, to form a particle-applied fingerprint; and then;
  ii) subjecting the material forming the particulate-applied fingerprint to mass spectrometry so as to detect the presence or absence of the residue.

In one exemplary embodiment, the method comprises use of materials, for example, metals, metal oxides, metal nitrides and carbon, that can be used (1) as agents for visualizing fingerprints, either by themselves or combined with or embedded within a vehicle, for example a silica vehicle, and (2) as a matrix for interrogating (analyzing) prints using a matrix-assisted mass spectrometric technique. The mass spectrometry technique is used to identify the presence or absence of substances such as one or more endogenous compounds or metabolites, exogenous compounds or metabolites and/or contact residues that the fingerprint includes. In one exemplary embodiment, the mass spectrometric technique is selected from (1) MALDI-TOF-MS, (2) SALDI-TOF-MS and (3) combinations thereof.

The fingerprint to which the method is applied can be a print that has been lifted from a surface using lifting tape.

In one exemplary embodiment, the particulate matter is hydrophobic to facilitate application and contacting of the particulate matter to a fingerprint.

It will be understood by skilled artisans that the term "fingerprint" includes reference to a partial print and/or to prints of other body parts and that, for example, a portion of a fingerprint to which the particulate matter has been applied can be subjected to mass spectrometry. A print can be lifted from its underlying surface prior to the application of mass spectrometry, and the term "fingerprint" accordingly includes lifted fingerprints. In exemplary embodiments, the fingerprint is lifted prior to application of the particulate matter. It is contemplated that the present invention includes methods in which step (ii) comprises the step of subjecting particulate matter that has acquired analyte from the print to the mass spectrometry. It is further contemplated that the present invention includes methods in which step (ii) comprises the step of subjecting both fingerprint material and particulate matter to the mass spectrometry.

It will be understood by those of ordinary skill that the terms "sample" and/or "analyte" in the context of the present invention can be taken to mean a print, a sample taken from a print and/or a residue present on or included in the print or the like.

In some exemplary methods of the present invention, a fingerprint is lifted from a surface and applied with the particulate matter (processing agent), whether before or after lifting, and the lifted fingerprint (at least, material comprised in the print) is then placed in a mass spectrometry apparatus. In other exemplary methods, a print is made directly on a sample support and, after application of the processing agent to the print, the sample support is placed in the mass spectrometric apparatus.

In one exemplary embodiment, the method further comprises the step, of locating and/or visualizing the fingerprint and interrogation of the print using the above-described mass spectrometry technique, for example, MALDI-TOF-MS and/or SALDI-TOF-MS.

According to an aspect of the present invention, there is provided a method of determining the presence of a residue within a fingerprint located on a surface, the method comprising the steps of:
 i) applying to the fingerprint a processing agent, for example, particulate matter comprising a material selected from a metal, metal oxide, metal nitride, a carbon particle and combinations thereof;
 ii) subjecting the fingerprint to mass spectrometry to detect the presence or absence of the residue.

As previously stated, therefore, the present invention relates to detection, optionally including quantification, of residues within fingerprints. The term "residue" refers to any material for which it is desired to detect, in particular, pre-selected compounds. The residue is, or may be, within (i.e., included) in a fingerprint; that is, the material that constitutes the fingerprint contains, or is suspected of containing or may contain, the residue.

In one exemplary embodiment, the particulate matter is hydrophobic. In one exemplary class of methods, the particulate matter can be used in combination with other matrix agents and/or other fingerprint detecting agents.

Exemplary embodiments of the present invention provide a method that enables detection of (1) an endogenously produced substance, e.g., proteins, lipids, DNA, peptides and/or endogenously derived metabolites, that is present as a residue included in a fingerprint; (2) an exogenous compound or metabolite that is present as a residue included in a fingerprint; and/or (3) a contact residue that is present on or within a fingerprint. Examples of the types of residues include, but are not limited to: (1) squalene and cholesterol; (2) cocaine and its metabolites and nicotine and its metabolite; (3) ballistic residues from, for example, firearms and/or explosives; and (4) residues from handling drugs of abuse (narcotics), e.g., cocaine.

In one exemplary embodiment, the method also enables the detection of contact residues that are co-deposited onto surfaces together with endogenously derived components (i.e., endogenous metabolites and/or exogenous metabolites).

The method described herein generally does not require the complicated extraction procedures prior to analysis associated with conventional techniques and further provides lower limits of detection.

One exemplary class of methods seeks to determine the presence or absence of a predetermined substance. According to such exemplary embodiments, the mass spectrum is examined for the presence of one or more peaks associated with the predetermined substance. Another exemplary class of methods seeks to identify one or more substances in a print by comparing peaks in the mass spectrum with a database or library of peaks. Both classes of methods can be performed in combination.

In one exemplary embodiment, the method comprises detection and/or identification of a residue included in a fingerprint that has been directly deposited onto a MALDI-TOF-MS or SALDI-TOF-MS sample support prior to application of the particulate matter. In one alternative exemplary embodiment, the method comprises the step of detecting the presence or absence of a residue within a fingerprint that has been lifted using a lifting means, for example, lifting tape or the like, from a surface. The surface can be the site of deposition of the fingerprint at, for example, a crime scene or the like. The method can comprise contacting the lifted fingerprint with a MALDI-TOF-MS or SALDI-TOF-MS sample support prior to application of the particulate matter.

The method can alternatively comprise the step of contacting the fingerprint with the particulate matter prior to application of lifting means, for example, lifting tape or the like, to the fingerprint. In one exemplary embodiment, a surface is first dusted to locate a latent print. Such a step is followed by lifting the dusted print with lifting tape. The print, located on the lifting tape, is then applied to a MALDI or SALDI target plate (sample support) prior to MS analysis.

A MALDI-TOF-MS or SALDI-TOF-MS sample support can be a plate, for example, a stainless steel plate, that is designed to fit into an MS system. The plate can comprise a well or plurality of wells to which a sample (e.g., a fingerprint, such as a lifted fingerprint) is added. In one exemplary embodiment, the prints are semi-solid deposits present on a sticky surface of the lifting tape.

The method can be employed qualitatively to determine the presence or absence of a residue and/or quantitatively to determine the amount of a residue. Furthermore, in one exemplary embodiment, the method can be used to visualize or image the fingerprint. Such a visualization or imaging can enable the "owner" of the fingerprint to be identified. To aid in the visualization of the fingerprint, preferably the particle further comprises a dye, for example, a fluorescent or colored dye. Appropriate dyes will be known to those skilled in the art, but can include, for example, rhodamine 6G or the like.

In one aspect, the present invention also provides the use of particulate matter comprising metal, metal oxide and/or carbon for the detection of a residue or residues on a fingerprint in a matrix-assisted mass spectrometry technique.

In one aspect of the present invention, there is provided the use of a matrix-assisted mass spectrometry technique in the identification of residues included in a fingerprint. Particularly, there is provided use of a MALDI-TOF-MS and/or SALDI-TOF-MS technique for detecting a residue in a fingerprint. The residue can be an endogenous residue (e.g., an endogenous substance or metabolite, for example, squalene or an exogenous metabolite, for example, a drug or a drug metabolite), and/or a "contact" residue, for example, ballistic residues from, typically, explosives or firearms. In one exemplary embodiment, a MALDI-TOF-MS technique and/or SALDI-TOF-MS technique can be used with fingerprint imaging agents that can be used to detect (particularly visualize) fingerprints. Examples of conventional fingerprint agents include aluminum, Magneta Flake and commercial white powder. In one exemplary embodiment, suitable matrix agents are used in the MALDI-TOF-MS/SALDI-TOF-MS technique to assist in the desorption/ionization process. Examples of conventional matrix agents include, for example, 2,5-Dihydroxybenzoic acid (DHB or DHBA) and α-cyano-4-hydroxy cinnamic acid (α-CHCA).

In an alternative exemplary embodiment, the use of MALDI-TOF-MS and/or SALDI-TOF-MS comprises the use of a particulate matter that comprises a material selected from (1) metal; (2) metal oxide (3) metal nitride and (4) carbon as a matrix agent. The particulate matter can further comprise additional features that are described herein. The particulate matter typically can also be used as an agent for detecting and/or imaging a fingerprint. In one exemplary embodiment, the fingerprint has a residue within it (i.e., included in it.). In one exemplary embodiment, the particulate matter can be used in combination with other matrix agents or materials (also known sometimes as matrix assistance agents and/or matrix enhancing agents). In one exemplary embodiment, the use can further comprise the identification of the residue.

According to a first aspect of the present invention, a method of determining the presence of a residue within a fingerprint includes the step of: (a) using a matrix-assisted mass spectrometry technique to determine the presence of the residue within the fingerprint.

According to the first aspect, the matrix-assisted mass spectrometry technique can comprise MALDI-TOF-MS and/or SALDI-TOF-MS. According to an alternative exemplary embodiment of the first aspect, the matrix-assisted mass spectrometry technique can comprise MALDI-TOF-MS-MS and/or SALDI-TOF-MS-MS. The method can include the step of: (b) visualizing and/or imaging the fingerprint. The residue can comprise an endogenous residue. The endogenous residue can comprise an endogenous metabolite and/or an exogenous metabolite. For example, the endogenous metabolite can comprise squalene, while the exogenous metabolite can comprise a metabolite of nicotine. The metabolite of nicotine can comprise, for example, cotinine. The residue can comprise a contact residue, such as, for example, a narcotic. The narcotic can comprise, for example, cocaine. At least one endogenous residue and at least one contact residue can be co-deposited within the fingerprint.

According to the first aspect, the method can include the steps of: (c) applying particulate matter to the fingerprint that is configured to (i) act as a matrix in the matrix-assisted mass spectrometry technique and (ii) aid at least one of detection and imaging of the fingerprint, to form a particulate-applied fingerprint; and (d) subjecting material forming the particulate-applied fingerprint to mass spectrometry to detect one of the presence and absence of the residue. The particulate matter can be hydrophobic. For example, the particulate matter can comprise hydrophobic silica particles. The particulate matter can comprise a metal, metal nitride, metal oxide or carbon. The metal oxide can comprise titanium oxide, iron oxide (magnetite), haematite or combinations thereof. The carbon can comprise carbon black, a fullerene compound, carbon nanotubes, graphite, an analog thereof or combinations thereof. The metal can comprises aluminum, iron or combinations thereof.

According to the first aspect, the particulate matter can comprise hydrophobic silica particles, and metal, metal nitride, metal oxide or carbon particle can be embedded within the hydrophobic silica particles. The average diameter of the hydrophobic silica particles can be less than or equal to about 100 μm. For example, the hydrophobic silica particles can comprise an average diameter of from about 10 to about 90 μm. Alternatively, the hydrophobic silica particles can comprise an average diameter of from about 45 to about 65 μm. However, the hydrophobic silica particles can comprise an average diameter of from about 65 to about 90 μm. The average diameter of the hydrophobic silica particles can be less than or equal to about 1 μm. For example, the hydrophobic silica particles can comprise an average diameter of about 200 to about 900 nm. Alternatively, the hydrophobic silica particles can comprise an average diameter of about 300 to about 600 nm. However, the hydrophobic silica particles can comprise an average diameter of about 400 to about 500 nm. The particulate material can comprise a dye molecule. The dye molecule can comprise one of fluorescent or colored. The dye molecule can be embedded within a hydrophobic silica particle. The particulate matter can be one of magnetic or paramagnetic. The fingerprint can be lifted from a site of deposition of the fingerprint using a lifting tape and contacted with a mass spectrometry sample support, after the particulate matter is applied to the fingerprint.

According to a second aspect of the present invention, a combination of a fingerprint lifting tape and a particulate matter, wherein the particulate matter includes a material that is configured to (i) act as a matrix agent in a matrix-assisted mass spectrometry technique and (ii) aid in at least one of detection and imaging of a fingerprint. The material is applied to a fingerprint to form a particulate-applied fingerprint. According to the second aspect, the particulate matter can be hydrophobic.

According to a third aspect of the present invention, a matrix-assisted mass spectrometry technique can be used to determine a residue within a fingerprint. The matrix-assisted mass spectrometry technique can be MALDI-TOF-MS, SALDI-TOF-MS or combinations thereof.

According to a fourth aspect of the present invention, a method of determining the presence of a residue within a fingerprint includes the steps of: (a) using a matrix-assisted mass spectrometry technique to determine the presence of the residue within the fingerprint, wherein the matrix-assisted mass spectrometry technique comprises one of MALDI-TOF-MS and SALDI-TOF-MS; (b) forming a particulate-applied fingerprint by applying particulate matter to the fingerprint that is configured to (i) act as a matrix in the matrix-assisted mass spectrometry technique and (ii) aid at least one of detection and imaging of the fingerprint; and (c) subjecting material forming the particulate-applied fingerprint to mass spectrometry to detect one of the presence and absence of the residue.

BRIEF DESCRIPTION OF THE DRAWINGS

Other objects and advantages of the present invention will become apparent to those skilled in the art upon reading the following detailed description of preferred embodiments, in conjunction with the accompanying drawings, wherein like reference numerals have been used to designate like elements, and wherein:

FIGS. 1A-1D are pictures illustrating fluorescent scans of fingerprints deposited on and lifted from a glass slide using rhodamine 6G as contact agent (λex 543 nm, λem 590 nm), wherein FIG. 1A illustrates latent fingerprints deposited onto a microscope slide (upper and lower with Rhodamine 6G, the center is a blank control), wherein FIG. 1B illustrates the fingerprints from FIG. 1A developed with "Sunderland White" fingerprint powder ($TiO_2$-embedded hydrophobic silica particles), wherein FIG. 1C illustrates residual of the prints from FIG. 1B after lifting with commercial fingerprint lifting tape, and wherein FIG. 1D illustrates the lifted fingerprints from FIG. 1B on the commercial lifting tape, in accordance with an exemplary embodiment of the present invention.

FIGS. 4A and 4B are graphs illustrating a comparison of matrix material for detecting cocaine on spiked fingerprints applied directly onto a metal MALDI-TOF-MS plate, in which the lower trace of FIG. 4A was obtained when using 2,5-dihydroxybenzoic acid (DHB) at 10 mg ml$^{-1}$ and the upper trace of FIG. 4A was obtained with magnetic hydrophobic silica particles, wherein FIG. 4B is a graph that illustrates spectral intensities at m/z 304.5 of fingerprints deposited onto metal target plates and dusted with the three powders both in the presence and absence of cocaine, in accordance with an exemplary embodiment of the present invention.

FIGS. 10A and 10B are graphs illustrating mass spectra for squalene and cholesterol standards, in which FIG. 10A illustrates MALDI-TOF-MS for squalene standard and FIG. 10B illustrates MALDI-TOF-MS for cholesterol standard, in accordance with an exemplary embodiment of the present invention.

DETAILED DESCRIPTION OF THE PREFERRED EMBODIMENTS

Figure 1:

The present invention relates to use of mass spectrometry in fingerprint residue analysis. Specifically, the present invention relates to the use of a matrix-assisted mass spectrometry technique, for example, Matrix-Assisted Laser Desorption/Ionization Mass Spectrometry Time-Of-Flight Mass Spectrometry (MALDI-TOF-MS) and/or Surface Assisted Laser Desorption/Ionisation Time-Of-Flight Mass Spectrometry (SALDI-TOF-MS), in the analysis of fingerprint residues.

As stated previously, the term "residue" refers to any material for which it is desired to detect, in particular, pre-selected compounds. The residue is, or may be, within (i.e., included in) a fingerprint, that is, the material that constitutes the fingerprint contains, or is suspected of containing or may contain, the residue.

In one aspect of the present invention, there is provided a method for determining the presence of a residue on a fingerprint, the method comprising the steps of: (i) applying a particulate matter to a fingerprint, the particulate matter having the following properties: (1) it is suitable for use as a matrix agent in a matrix-assisted mass spectrometry technique, and (2) it is suitable for use as an agent for detecting and/or imaging a fingerprint; and (ii) subjecting the fingerprint to mass spectrometry to detect the presence or absence of the residue.

Preferably, the particulate matter is hydrophobic. The present invention further includes methods for analyzing a hydrophobic substrate by matrix-assisted mass spectrometry, in which the matrix is hydrophobic. In one exemplary embodiment, the method comprises, e.g., prior to step (ii), the step of preparing at least one calibration standard for use in calibrating the mass spectrometric technique. In an exemplary embodiment, the method comprises the step of analyzing the outcome of step (ii) to, for example, determine whether a specific residue (e.g., nicotine) is present in the fingerprint.

As stated above, the skilled artisan will understand that the term "fingerprint" includes reference to a partial print and/or to prints of other body parts and that, for example, a portion of a fingerprint to which the particulate matter has been applied may be subjected to mass spectrometry. A fingerprint can be lifted from the surface prior to the application of mass spectrometry, and the term "fingerprint" accordingly includes lifted fingerprints. In accordance with an exemplary embodiment, the fingerprint is lifted prior to application of the particulate matter. It is contemplated that the present invention includes methods in which step (ii) comprises the step of subjecting the particulate matter to the mass spectrometry. It is further contemplated that the present invention includes methods in which step (ii) comprises the step of subjecting both the fingerprint and the particulate matter to the mass spectrometry. In one exemplary class of methods, step (i) comprises the step of immersing an article on which a print is or may be deposited in a liquid medium comprising the particulate matter before being removed. The length of immersion is not critical and may vary from about 15 minutes to about 12 hours or longer. The print can then be lifted from the article using lifting tape.

It will be understood by those of ordinary skill that the terms "sample" and/or "analyte" in the context of the present invention can be taken to mean a fingerprint and/or a residue present on or within the fingerprint, whether deposited directly or alternatively lifted from a surface using lifting means, for example, lifting tape or the like.

In one exemplary embodiment, the mass spectrometric technique can be MALDI-TOF-MS and/or SALDI-TOF-MS. In short, MALDI-TOF-MS requires the mixing of samples with matrix molecules and the application of the matrix material to a sample or the like. The MALDI-target is introduced into the ion source of a mass spectrometer that is under a high vacuum. A strong electrical field is applied between the sample and the extraction plate(s). A laser is fired onto the sample, resulting in a desorption event due to absorbance of the laser energy by the matrix molecules.

Thus, the present invention comprises methods that utilize a material that is suitable as a matrix material in a MALDI-TOF-MS and/or SALDI-TOF-MS process. It is considered that the particulate matter contains a material that can absorb energy from the laser and transfer it to an analyte that is comprised in the sample. In the present invention, the analyte can be a substance forming a residue or residues within a fingerprint. The transfer of energy to the analyte results in ionization of the analyte and acceleration through the mass analyzer. When MALDI-TOF-MS is used in this way, i.e., with transfer of ions to a sample (analyte), it is known as positive ion detection.

In an exemplary embodiment, the transfer of electrons can be from the analyte to the particulate matter. In such an exemplary embodiment, the MALDI-TOF-MS (or SALDI-TOF-MS) is considered to be running in a negative ionization mode.

If the sample (for example, the residue or suspected residue on or within the fingerprint) is believed to have functional groups that readily accept a proton (H+) then positive ion detection can be used. If the sample (for example, the residue or suspected residue on or in the fingerprint) is suspected to have functional groups that readily lose a proton, then negative ion detection can be used.

The method can enable the presence of (i) endogenous residues, for example endogenous metabolites and exogenous metabolites, and (ii) contact residues included in the fingerprint to be determined. The endogenous metabolites and "contact" residues can be co-deposited within the fingerprint. The method can further enable identification of the residue.

One exemplary class of methods can be used to detect and/or identify endogenous residues, for example residues that have been produced as a result of metabolism of a substance by a person's body. The endogenous residues can include endogenous metabolites (e.g., metabolites of molecules produced by the body) or exogenous metabolites (e.g., metabolites of molecules ingested or transferred into the body and subsequently metabolized by the body).

Other examples of endogenous residues that may be identified by the method include, for example, endogenous substances (e.g., squalene, cholesterol, waxes and esters, steroids, e.g., estrogens and testosterone, and markers of gender and health) that can be secreted through skin pores and deposited with other chemicals within the fingerprint. The method can also be used to detect the metabolites and conjugates of the aforementioned. Examples of endogenous residues can also include exogenous metabolites, for example, drug and their metabolites including drugs of abuse and their metabolites, prescribed drugs and metabolites and compounds derived from dietary sources or breakdown products of the same. The method can also be applied to the proteomic or genomic analysis of the cells (e.g., shed skin cells) or DNA respectively located within the developed print. The method can also be used to detect other contact residues, for example, illegal drugs, e.g., narcotics, explosive material, for example, material used in bomb making processes, and residue from the use of a fire arm.

In a further aspect of the present invention, there is provided the use of a MALDI-TOF-MS and/or SALDI-TOF-MS technique for detecting and/or identifying a residue included in a fingerprint. The residue can be an endogenous residue and/or a "contact" residue, for example, ballistic residues from, for example, explosives or firearms. In one exemplary embodiment, the residue can be a "contact" residue, that is to say, a residue that has been transferred to a person's hand through contact with a substance and subsequently transferred to a surface with a person's fingerprint. The detection of such residues is of particular interest to law enforcement agencies and could prove to be a critical piece of forensic evidence. In one exemplary embodiment, a particulate matter that comprises a material selected from metal, metal oxide, carbon and combinations thereof can be used to contact the fingerprint and act as a matrix in the MALDI-TOF-MS apparatus.

In an alternative exemplary embodiment, the fingerprint can be contacted by a fingerprint developing agent that can be used to detect fingerprints. Examples of conventional fingerprint agents include aluminum, Magneta Flake and Commercial White and the like. The method can then use a MALDI-TOF-MS matrix agent, for example, DHBA (2,5-dihydroxybenzoic acid) or α-cyano-4-hydroxy cinnamic acid (α-CHCA) or another matrix agent that can be, e.g., the particulate matter as described herein.

The method of the present invention can be used to analyze a variety of residues that can be found on a fingerprint. Thus, in an exemplary embodiment, the method can be used to develop and analyze latent fingerprints from smokers. It is well established that nicotine is extensively metabolized to cotinine in vivo (as described in, for example, J. Hukkanen, P. Jacob and N. L. Benowitz, "Metabolism and Disposition Kinetics of Nicotine," Pharmacology Reviews, 57 (2005), pages 79-115 (hereinafter, the "Hukkanen reference"), and there is evidence that both nicotine and cotinine are excreted together in sweat (as described in, for example, the Kidwell reference). FIGS. 11 and 12A-12C and 12 illustrate graphs 1100, 1205, 1210 and 1215, respectively, demonstrating that the particulate matter as described herein, particularly, hydrophobic silica particles containing a substance selected from metal, metal nitrides, metal oxides and carbon can be used as developing agents to visualize latent fingerprints from smokers, and that such prints can be analyzed by MALDI-TOF-MS either directly on a suitable surface or following lifting from the surface, to detect nicotine and/or its metabolites.

In one exemplary embodiment, the method described herein can be used to detect or determine whether a person has handled or ingested drugs of abuse, for example, cocaine or the like.

In other exemplary embodiments, the method described herein can be used as part of personnel screening to determine whether a person is, for example, a smoker or has taken drugs of abuse, such as, for example, cocaine or the like.

While the exemplary method described herein can be used to identify whether a particular residue is present on or within a person's fingerprint, the results are not to the highest level of accuracy and can, therefore, be unacceptable currently to the standard required by, for example, criminal courts. In such circumstances, e.g., if the method is being carried out for the purpose of obtaining evidence for use in a court of law, the method can further comprise the use of tandem mass spectrometry, that is to say, carrying out a further mass spectrometry technique, for example, to provide structural information for a compound present in a residue in a fingerprint.

Thus, in one exemplary embodiment, the method comprises the step of subjecting a fingerprint and/or particulate matter to MALDI-TOF-MS-MS and/or SALDI-TOF-MS-MS. MALDI-TOF-MS-MS/SALDI-TOF-MS-MS can fragment specific sample ions inside a mass spectrometer, and, therefore, provide further structural information about a residue. Thus, in one exemplary embodiment, the method comprises the step of identifying the resulting fragment ions. Such structural information can be useful in certain situations, for example, as mentioned above for the example of obtaining evidence in a court of law.

Method and uses described herein can be used in a variety of applications. In one exemplary embodiment, the methods and uses can be utilized as part of a personnel screening process, for example, by employees, to determine whether a person smokes or is an abuser of illegal drugs. In an exemplary embodiment, the methods and uses can be utilized as part of a "drug-testing" process in the field of, for example, professional or amateur sports.

In one exemplary embodiment, the method described herein can be used to detect residues, either contact residues or endogenous residues, that contain illegal or banned substances and/or metabolites thereof. In particular, the method can be used to test professional and/or amateur sportspeople at sports events and/or random tests for the presence or absence of banned substances in a residue taken from the person's fingerprint. The advantage of using the present method over currently used methods is that analysis is performed directly on an individual's own fingerprint, and, therefore, substitution of a sample is not possible, as is the case with currently used methods of urine and saliva samples followed by drug analysis screens.

The use of MALDI-TOF-MS and/or SALDI-TOF-MS to detect and/or identify a residue on a fingerprint has not previously been considered, and, therefore, the use of these techniques to detect and/or identify a residue on a fingerprint forms part of the present invention. The use can comprise contacting of a particulate matter as described herein to a fingerprint. Alternatively, the use can comprise contacting of a conventional fingerprint detecting agent to a fingerprint. In such an exemplary embodiment, the use can further comprise use of a matrix agent that is conventionally known in a mass spectrometry step. Alternatively, the particulate matter as described herein can be used as a matrix agent in a mass spectrometry step.

The methods and uses of exemplary embodiments of the present invention can also be used at points of entry into a country to test travelers for presence of residues that may suggest, e.g., illegal drug handling or the taking or handling of prohibited substances, e.g., firearms and ballistics.

As described above, the methods can be used as forensic evidence of, for example, drug or ballistic handling for use in a court proceeding, e.g., a criminal court.

Particulate Matter

The present invention utilizes particulate matter that can be contacted with a fingerprint and that can subsequently be used in a mass spectrometry technique to determine whether a residue is present on the fingerprint.

The particulate matter preferably comprises a material selected from metal, metal nitride, metal oxide, carbon and combinations thereof.

In one exemplary embodiment of the present invention, the particulate matter can comprise hydrophobic silica particles. One exemplary class of hydrophobic silica particles is obtainable by the following method: a method (designated method A) for preparing hydrophobic silica particles is provided that comprises the step of reacting together in a single step a mixture of (1) silane ether monomers, for example, a alkoxysilane and (2) organically substituted silane ether monomers, for example, a phenyl modified silicate, with a hydrolyzing agent, e.g., an alkali.

Thus, the exemplary method can comprise the use of alkoxysilane monomers. The method can comprise the use of tetraalkoxysilanes (abbreviated herein to "TAOS"). The TAOS's can be selected from TEOS (tetraethoxysilane) or TMOS (tetramethoxysilane).

In one exemplary embodiment, the mixture further comprises a water miscible solvent, for example, ethanol, and also water. The method can be carried out at ambient temperature. The duration of the reaction is not critical. The reaction between the tetraalkoxysilane (TAOS) monomers and phenyltriethoxysilane (PTEOS) monomers can be performed overnight or for an equivalent time period, that is to say, for between about 12 and about 18 hours. The length of the reaction has an effect on the size of silica particles produced. For example, the earlier a reaction is stopped, the smaller the particles that are formed. Therefore, the reaction can be performed over a period of less than 12 hours, e.g., between about 6 and about 12 hours. The reaction can be alternatively performed for longer than 18 hours. If desired, the temperature can be elevated (or reduced) and the duration of the reaction reduced (or increased).

The hydrolyzing agent, such as an alkali, acts as a catalyst within the reaction. Preferably, such as catalyst is a hydroxide, for example, ammonium hydroxide. The catalyst can instead be an acid. Examples of acids include, but are not limited to, mineral acids, e.g. hydrochloric acid. In the present method, the reaction comprises an acid induced hydrolysis.

The silane ether monomer, for example, a TAOS, and the organically substituted silane ether monomer, e.g., PTEOS monomers, can be used, for example, in ratios (PTEOS:TAOS) of from about 2:1 to about 1:2, e.g., about 4:3 to about 3:4, and, in particular, about 1.2:1 to about 1:1.2. In one exemplary class of methods, the ratio is at least about 1:1, e.g., up to 1:5, for example about 1:2. In another exemplary class of methods, the PTEOS:TAOS ratio is preferably about 1:1 v/v. It will be understood by skilled artisans that, where one or both of the TAOS and PTEOS are replaced by alternative reagents, the same or substantially same ratios can be used.

The hydrophobic silica particles produced by the above method tend to be predominantly nanoparticles, that is to say, of an average diameter of approximately 200 nm to about 900 nm, for example, about 300 nm to about 800 nm, and, in particular, about 400 nm to about 500 nm. These nanoparticles can be subsequently processed to form microparticles that can be considered to be coalesced nanoparticles. The microparticles can be produced using a method that, for example, comprises the following steps:

i) centrifuging a suspension of particles;
ii) transferring the suspension of hydrophobic silica particles into an aqueous phase;
iii) extracting the suspension from the aqueous phase into an organic phase;
iv) evaporating the organic phase; and
v) crushing and sieving the product obtained in step (iv).

The organic phase preferably comprises an organic solvent that is non-polar or has low polarity. The organic phase can be dichloromethane or another suitable organic solvent, for example, alkanes, e.g., hexane, toluene, ethyl acetate, chloroform and diethyl ether.

Alternatively, hydrophobic silica microparticles can be obtained from a reaction product containing hydrophobic silica nanoparticles using a method comprising the steps of:

(a) centrifuging the reaction product; and
(b) washing the reaction product in a fluid.

The method can comprise repeating steps (a) and (b) a plurality of times. Preferably, the fluid comprises an aqueous:solvent mixture and can be a water:organic solvent mixture. For example, the organic solvent can comprise ethanol. Preferably, the initial fluid comprises a mixture of water and organic solvent at a ratio of from about 60 (water):40 (solvent) to about a 40:60 v/v mixture. In other exemplary embodiments, the solvent can be, for example, dimethylformamide, n-propanol or iso-propanol.

The proportion of solvent in the mixture can increased between the initial washing (i.e. suspension) (step (b)) and the final washing (suspension). To obtain microparticles that are coalesced nanoparticles, the final suspension is dried. The microparticles can then be sieved. Once sieved, the microparticles are ready for application as a fingerprint developing agent for example in step (i) of the present method for detecting a residue in a fingerprint.

The microparticles can be considered to be aggregates of smaller silica nanoparticles. In this exemplary embodiment, the microparticles are of sufficient size to be efficiently captured using face masks, and, hence, are not inhaled. Thus, in one exemplary embodiment, the silica microparticles can comprise an average diameter of at least about 10 µm, typically at least about 20 µm. For example, the microparticles can have an average diameter of from about 30-90 µm. In some exemplary embodiments, the microparticles can have an average diameter of between about 45-65 µm or from about 65 to 90 µm. According to an exemplary embodiment, the particulate matter comprising the microparticles can be a dry particulate matter.

In one exemplary class of methods, the particulate matter comprises hydrophobic silica nanoparticles. Hydrophobic silica nanoparticles can be isolated using a method that comprises the steps of centrifuging a reaction product from Method A and suspending it in an aqueous:solvent mixture. The aqueous:solvent mixture is a first aqueous:solvent mixture and is preferably a 50:50 mixture. The method can further comprise the steps of removing the reaction product from the first aqueous:solvent mixture, centrifuging it, and suspending it in a second aqueous:solvent mixture. Preferably, the second aqueous:solvent mixture has a similar or substantially similar proportion of solvent and aqueous component as the first mixture. The aqueous solution that forms part of the aqueous:solvent mixture is preferably water. The solvent that makes up the solvent portion of the aqueous:solvent mixture is, for example, a water-miscible solvent, for example, ethanol. Alternatively, dimethylformamide, n-propanol or iso-propanol can be used.

The step of suspending the reaction product in an aqueous:solvent mixture can be repeated a plurality of times. Preferably, the composition of the aqueous:solvent mixture is altered to increase the proportion of solvent in the aqueous:solvent mixture over the course of repeated suspensions. Preferably, the method comprises, in a final step, the step of suspending the reaction product in an aqueous:solvent "mixture" which is 0% aqueous:100% solvent. The total number of suspensions is typically from about 3 to about 10, e.g., 4, 5, 6, 7, 8 or 9. After each suspension, except the final suspension, the suspensions can be centrifuged. The nanoparticles can be stored in the final ethanolic suspension. It will be appreciated by those of ordinary skill that centrifugation is one exemplary method of isolating the nanoparticles from the aqueous:solvent mixture and other suitable separation techniques can also be use.

In one exemplary embodiment, the particulate matter comprises hydrophobic silica nanoparticles. One exemplary class of particulate matter is a suspension of hydrophobic silica nanoparticles in a fluid. The fluid can be an ethanolic aqueous suspension. Alternatively, other organic solvents can be used in place of ethanol in the suspension, e.g., dimethylformamide, n-propanol or iso-propanol.

The physical nature and dimensions of the particles comprised within the particulate matter can be determined using Scanning Electron Microscope (SEM) and Transmission Electron Microscope (TEM) scans. The particles are in the form of amorphous silica that is commonly used as an anti-caking agent in a variety of food products, and as an anti-caking agent and as an excipient in pharmaceuticals for various drug and vitamin preparations, as described in, for example, J. Cao, Y. Wang, J. Yu, J. Xia, C. Zhang, D. Yin and U. O. Häfeli, J. Magnetism and Magnetic Materials (2003) (hereinafter, the "Cao reference").

Thus, in a preferred exemplary embodiment, the particulate matter comprising nanoparticles is applied to a fingerprint or surface in a suitable liquid medium. For example, the liquid medium can be an aqueous:solvent mixture. The solvent can be a water-miscible solvent. In one exemplary embodiment, the aqueous component comprises water. The solvent can be, for example, a water miscible solvent, i.e., 100% miscible in all proportions in water. In one exemplary embodiment, the solvent comprises ethanol. The water:solvent ratio ranges from about 99.9:0.1 (water:solvent) to about 96:4 (water:solvent). The level of solvent preferably is not greater than about 4%, since a higher level of solvent can result in the fingerprints becoming dissolved or their definition reduced. It is preferable to include at least a trace amount of solvent to ensure that the nanoparticles remain as discrete particles and do not coalesce to form aggregates.

Alternatively, the particulate matter can comprise hydrophobic silica particles can be obtained using conventional methods known to those of ordinary skill in the art, such as described in, for example: Tapec et al., Nano Sci. Nanotech, 2002, Vol. 2, No. 3/4, pages 405-409; E. R. Menzel, S. M Savoy, S. J. Ulvick, K. H. Cheng, R. H. Murdock and M. R. Sudduth, "Photoluminescent Semiconductor Nanocrystals for Fingerprint Detection," Journal of Forensic Sciences (1999), pages 545-551; and E. R. Menzel, M. Takatsu, R. H. Murdock, K. Bouldin and K. H. Cheng, "Photoluminescent CdS/Dendrimer Nanocomposites for Fingerprint Detection," Journal of Forensic Sciences (2000), pages 770-773.

In one exemplary embodiment, the particulate matter comprises hydrophobic silica particles into which a dye has been incorporated. In an exemplary embodiment, the dye to be incorporated into the particle can be, for example, a colored or a fluorescent dye. Examples of dyes include, but are not limited to, fluorescein derivatives, for example, Oregon Green, Tokyo Green, SNAFL, and carboxynapthofluorescein, rhodamine (e.g., rhodamine B and rhodamine 6G) and analogues thereof, thiazole orange, oxazine perchlorate, methylene blue, basic yellow 40, basic red 28, and crystal violet and analogs thereof. It is considered that dyes that are positively charged, for example, rhodamine, are better incorporated when PTEOS is used in the method than dyes that comprise anionic or cationic groups, such as carboxylic groups. Examples of other dyes that could be used in the present invention include those which possess a planar aromatic substructure and positively charged functional groups (e.g., ethidium bromide and other DNA intercalating agents).

It can be advantageous for the particles to be magnetic or paramagnetic. For example, magnetizable microparticles can easily be dusted over fingerprints, using a magnetic wand or other appropriate tool. In a preferred exemplary embodiment of the present invention, therefore, magnetic or paramagnetic subparticles are incorporated into hydrophobic silica particles. In an exemplary embodiment of the present invention, the particles are magnetizable, e.g., magnetic or paramagnetic. The magnetic and/or paramagnetic particles can be any suitable magnetic or paramagnetic component, for example, metals, metal nitrides, metal oxides and carbon. Examples of magnetic metals include, but are not limited to, iron, whilst examples of a metal oxide include magnetite and haematite.

In a further preferred exemplary embodiment of the present invention, the carbon comprises carbon black, carbon nanoparticles, a fullerene compound or graphite or an analog thereof. A fullerene compound is composed of at least 60 atoms of carbon (e.g., C60). Preferably, the carbon is in the form of carbon nanoparticles. Carbon nanoparticles can be in the form of, for example, carbon nanotubes (derivatized or underivatized). The carbon nanotubes can be multi-walled carbon nanotubes and/or single walled carbon nanotubes.

In one exemplary embodiment, the metal oxide is selected from titanium oxide ($TiO_2$), magnetite, haematite and combinations thereof. In an exemplary embodiment, the metal is selected from aluminum, iron and combinations thereof. However, it is considered that, in alternative exemplary embodiments, the skilled artisan will consider that alternative metal oxides and or metal nitrides can be used that assist in the desorption/ionization process of the MALDI-TOF-MS and/or SALDI-TOF-MS used in the present invention. Similarly, the skilled artisan will consider that other metals and/or forms of carbon that assist in the ionization process can be used in the particulate matter. The metal, metal oxide, metal nitride or carbon can be embedded within the particles of the particulate matter. The particles of the particulate matter preferably have an average diameter of $\leq 100$ μm, for example, a diameter of $\leq 1$ μm. In one exemplary embodiment, the particles can have an average diameter from about 10 nm to about 100 μm.

The hydrophobicity of the silica particles enhances the binding of the particles to the fingerprint. Thus, in one exemplary embodiment, the metal, metal oxide and/or carbon are incorporated in and/or embedded in a hydrophobic silica particle.

In those exemplary methods that involve a fingerprint, the particulate matter and fingerprint can be contacted together. It will be understood by those of ordinary skill that the term "fingerprint" in this context can refer to, for example, a fingerprint deposited on a surface or alternatively an "indirect" fingerprint that has been lifted from a surface using convention lifting means, for example lifting tape or the like.

Application of the particulate matter can be by way of a magnetic wand, and, in such an exemplary embodiment, the particulate matter is magnetic or paramagnetic. Such an embodiment has health and safety advantages as it reduces exposure by any personnel to particulate matter, particularly via inhalation. Alternatively, the article in which a print is deposited can be immersed in the liquid medium (i.e., suspension of nanoparticles) and then removed. The length of immersion is not critical and can vary from about 15 minutes to about 12 hours or longer.

In one exemplary embodiment, therefore, the particulate matter comprises hydrophobic silica particles that comprise magnetizable particles as described above.

One exemplary class of particulate matter comprises hydrophobic silica particles. The particles can be nanoparticles or microparticles or a combination thereof. In one exemplary embodiment, the silica microparticles have an average diameter of at least about 10 μm, for example, at least about 20 μm. The microparticles can have an average diameter of from about 30-90 μm. In some exemplary embodiments, the microparticles can have an average diameter of between about 45-65 μm or from about 65 to about 90 μm.

It is envisaged that nanoparticles that have an average diameter of from about 200 nm to about 900 nm can be used by the methods. Preferably, the nanoparticles can have an average diameter of between about 400 and about 500 nm. However, it is envisaged that particulate matter comprising nanoparticles that have a diameter that is from about 200 nm to about 900 nm, e.g., 200, 250, 300, 350, 400, 450, 500, 550, 600, 650, 700, 750, 800, 850 or 900 nm, can be used in the method.

The term "average diameter" can be taken to mean a "mean diameter" of particles typically formed from the methods of the present invention. As recognized by skilled artisans, the term "mean" is a statistical term that is essentially the sum of all of the diameters measured divided by the number of particles used in such measurements. The diameters of nanoparticles can be estimated from SEM pictures and the scale used in pictures, and for microparticles the diameter can be estimated from a combination of the sieve size, the results from particle size distribution measurements and from SEM pictures. One way a mean diameter can be determined is by using a Malvern MASTERSIZER™ (manufactured by Malvern Instruments Ltd.).

In one exemplary embodiment, the particulate matter can comprise a mixture of (1) hydrophobic silica particles as described herein, and (2) magnetic or paramagnetic particles, e.g., iron particles or the like.

In an exemplary embodiment, the particulate matter comprises hydrophobic silica particles that further comprise a molecule that aids in visualization and/or imaging of a fingerprint. In one exemplary embodiment, the hydrophobic silica particle comprises a dye molecule. Examples of dyes include, for example, rhodamine e.g. rhodamine 6G and derivatives thereof. The step of visualizing the fingerprints can be carried out using various methods known to those of ordinary skill in the art. For example, optical methods can be used, for example, a UV search light, optical scanner including a flat-bed optical scanner, a fluorescent scanner, a UV visible scanner and the like.

Materials and Methods

The Tecan LS300 scanner used according to an exemplary embodiment is from Tecan UK, Reading, Berkshire. A Kratos Axima-CFR MALDI-TOF-MS (Shimadzu Biotech, Manchester UK) system is used with Shimadzu metal target plates. The commercial matrix used is 2,5-dihydroxybenzoic acid (DHB) (10 mg ml−1 in 50:50 Acetonitrile:deionised water [$dH_2O$]). Carbon black suspension was obtained from Cabot Corp, Cheshire UK. All other chemicals are available from Sigma-Aldrich, Dorset UK, including the titanium dioxide in the form of anatase. The commercial dusting agents, fingerprinting brushes, magnetic wands and commercial lifting tape are available from Crime Scene Investigation Equipment Ltd. (formerly K9 Scenes of Crime Ltd.) Northampton, UK.

A calibration solution was prepared for use in the MALDI-TOF-MS system. Solutions of papaverine hydrochloride (10 mg/ml in $dH_2O$), and reserpine (5 mg/ml solution in dimethylformamide, DMF) were prepared. An aliquot of this papaverine solution (100 μl) was mixed with aliquots of the reserpine solution (200 μl) and $dH_2O$ (400 μl) and DMF (300 μl). A solution of 2,5-dihydroxybenzoic acid (DHB, 10 mg/ml) was also prepared in acetonitrile/water (50:50 v/v). The final calibrant solution was prepared by mixing together the 10 μl each of the DHB solution and the mixture of reserpine and papaverine. Aliquots (1 μl) of this solution were used in each experiment and the m/z for the molecular ions of the two standards was used to calibrate the system.

Preparation of Embedded Hydrophobic Silica Particles

The present example is an adaptation of the preparation of blank silica based nanoparticles (as described in the Cao reference), and 30 ml ethanol, 5 ml $dH_2O$, 2.5 ml of tetraethoxysilane and 2.5 ml phenyltriethoxysilane are mixed in a centrifuge tube. To this is added 2 ml ammonium hydroxide solution (28%) to initiate nanoparticle formation and the solution rotated overnight. The resulting particulate suspension is extracted repeatedly with methylene dichloride/water or ethanol/water (50:50 in both cases). The suspension is centrifuged (e.g., about 5 minutes at 3000 RPM). The supernatant is removed and 10 ml $dH_2O$ and the same volume of dichloromethane added. The suspension is rotated for a further 10 minutes, prior to the suspension being centrifuged again. The aqueous upper layer of the solution is removed and further aliquots of water and dichloromethane added. Such a process of rinsing and centrifugation is repeated about four times until no further water:dichloromethane can be added. After such time, the particles are dried down from the dichloromethane in an incubator at about 40° C.

Once dry, the particles are crushed in a mortar and pestle prior to being sieved to produce suitable particle sizes. The hydrophobic particles were sieved through brass test sieves with bronze mesh (such as those that can be obtained from Endecot Ltd., London UK) by hand. The particle size fractions used in the present example were below approximately 63 μm. A Malvern MASTERSIZER™ (Malvern Instruments Ltd., Malvern, UK) is used to verify the particle size distributions.

For titanium dioxide containing particles, 25 mg of titanium dioxide is added to the centrifuge tube, prior to the addition of the silanization reagents. For Carbon Black (CB) particles, 5 ml of a 1:2-1:100 fold dilution of the supplied carbon black suspension in water is added to the precursor solution in place of the $TiO_2$. For magnetic particles, particulate magnetite is prepared according to method described in, for example: J. J. Harburn, R. R. Ritter, C. D. Spilling, K. M. Miller, "Magnetically Responsive Particles and Embolic Materials using Coated Magnetically Responsive Particles," U.S. patent application Ser. No. 10/623,863, filed Jul. 21, 2003; and L. A. Harris, J. D. Goff, A. Y. Carmichael, J. S. Riffle, "Magnetite Nanoparticle Dispersions Stabilized by Triblock Copolymers," Chemistry of Materials, 15 (2003) page 1367, the entire contents of each of which are hereby incorporated by reference herein. 5 ml of this suspension in water is then added to the precursor solution in place of $dH_2O$.

Demonstration that Contact Residues are Effectively Lifted from Latent Fingerprints A fingertip was placed into a Rhodamine 6G ("Rh 6G"; 100 μg ml−1 in EtOH) solution. The finger was waved to evaporate off excess EtOH prior to deposition of a fingerprint onto a clean glass slide. Three prints were deposited, 2 with Rh 6G and a blank control. These were viewed using the Tecan LS300 scanner (λex 543 nm, λem 590 nm, gain 120). The prints were then dusted with hydrophobic microparticles of silica that had incorporated within them titanium dioxide, prior to being visualized under the same scanning conditions. They were then lifted using commercially available lifting tape (11.5 cm×6.5 cm) and both the residue on the glass slide and lifting tape scanned.

Experiment to Demonstrate MALDI-TOF-MS Detection of Lifted Contact Residue (Rhodamine 6G)

In this example, a few grains of Rh 6G powder were added directly to a fingertip, prior to deposition as a fingerprint on a glass slide as before, but no dusting agent was added. The fingerprint was then lifted using double-sided conductive tape and deposited onto a metal target. The conductive tape is suitable for use in the MALDI-TOF and was obtained from Shimadzu Biotech. The target plate was then placed inside the MALDI-TOF-MS system and the fingerprint was examined for the presence of Rh 6G. The resulting MS, with the detectable m/z for Rh 6G at approximately 444, was compared to that of a standard 1 μl of a 100 μml−1 solution in ethanol equivalent to 100 ng of dye deposited on a flat piece of tape.

Experiment to Demonstrate the Efficacy of Carbon Black Embedded with Silica Particles as Enhancing Agents in SALDI-TOF-MS The instrument response to cells with CB-embedded nanoparticles in the presence and absence of cocaine that was deposited onto circular cells/areas present on the surface of the metal target plate were studied. All results were performed in triplicate. Cocaine hydrochloride (1 μg dispensed as a 1 μl of a 1 mg/ml solution of ethanol) was added to 2 sets of wells. To the positive set, 1 μl of 10 mg ml−1 suspension of CB-embedded nanoparticles (matrix) was added to the cell. The other set was left as a control to show the response to cocaine without any matrix. A control of matrix in the absence of cocaine was also studied as were blank cells of the metal target. The cells were dried as previously described prior to analysis.

Detection of Cocaine Contact Residues by MALDI-TOF-MS

A small amount (a few grains) of cocaine hydrochloride was deposited onto a finger tip by placing the finger tip into the drug. The finger then made direct contact with a clean metal target plate thereby depositing a print on the surface of the target and the resulting print covered numerous cells/wells on the surface. The latent prints were then dusted with the hydrophobic silica particles embedded with magnetite, or commercial dusting agents. These were aluminum powder, MAGNETA FLAKE™ and white powder thought to contain titanium dioxide. A commercial magnetic wand was used to apply the two magnetic powers while a commercial brush was used for the non-magnetic powders. To prove the presence of cocaine on the fingerprint, commercial DHB matrix, 10 µl of 10 mg ml$^{-1}$ was mixed with 10 µl of 10 mg ml$^{-1}$ cocaine hydrochloride solution and 1 µl of this mixture was added to the wells of the MALDI target. The metal target was then dried in a heater box (Shimadzu/Kratos Instruments) and subsequently placed in the MS system.

Experiment to Demonstrate Effectiveness of TiO$_2$/PTEOS Particles for the Detection of Cocaine Residues on Lifted Fingerprints Blank and cocaine spiked fingerprints were deposited onto glass slides as described above. These were developed using TiO$_2$/PTEOS particles using a Zephyr fingerprinting brush. The prints were then lifted using commercial lifting tape and this was inverted and stuck print-side up to the MALDI target plate. The fingerprints were then interrogated for the presence or absence of cocaine by MS.

Detection of Cholesterol and Squalene from Fingerprints by Use of MALDI-TOF-MS, Using the Hydrophobic Particles as Enhancing Matrix A metal target plate was cleaned and dried. Twelve right hand index fingerprints were deposited onto the metal plate. These were then allowed to dry in an incubator at about 37° C. for about 1.5 hours. Each fingerprint was dusted with ten different formulations of hydrophobic particles prepared as described above. The agent embedded within the particles is shown in parentheses in each case. In addition, some of the resulting powders (1, 5, 6 and 8) were also subsequently thoroughly mixed with DHB to produce a 1% w/w formulation. These were used to determine whether the presence of this matrix improved the detection of squalene in the latent print following dusting and MALDI-TOF-MS. Four formulations of Black powder were used. These formulations had differing proportions of carbon black within them resulting from the initial synthesis. The numbers in parentheses refer to the ratio of carbon black to dH$_2$O used in the initial synthesis:

1. White powder A (titanium dioxide; 1.0% w/w DHB; powder)
2. White powder B (titanium dioxide)
3. Violet powder A (crystal violet)
4. Black powder A (1:10)
5. Black powder B (1:10, 1.0% w/w DHB: powder)
6. Violet powder B (crystal violet; 1.0% w/w DHB: powder)
7. Red fluorescent powder A (rhodamine 6G)
8. Red fluorescent powder B (rhodamine 6G; 1.0% w/w DHB: powder)
9. Black powder C (1:5)
10. Black powder D (1:2)

Each of the first ten prints was individually dusted with the correspondingly numbered powders 1-10 and the resulting prints were photographed with a digital camera (pictures not shown). They were then individually analyzed in MALDI-TOF-MS, including a print that had not been treated with dusting agent or matrix (print 12), and a print dusted with only dihydroxybenzoic acid (print 11).

Direct Detection of Cholesterol and Squalene by Use of MALDI-TOF-MS, Using the Hydrophobic Particles as Enhancing Matrices Solutions of cholesterol and squalene (both 2 mg/ml) were prepared in 100% ethanol and 500 µl aliquots of each solution were mixed together. Twenty-four spots (each of 0.5 µl) of this solution were dispensed onto a clean dry metal target and allowed to air dry for 2 hours. The wells were individually dusted with each formulation of eight hydrophobic powders (3 spots for each formulation). The formulations were identical to those described above:

1. Red Fluorescent Powder A
2. Black powder A
3. Black powder B
4. Violet powder A
5. Violet powder B
6. Red Fluorescent powder B
7. Black powder C
8. Black powder D Dusting was carried out as described above directly on the surface of the metal plate with each of the powders. A separate solution was also prepared by mixing 500 µl of the cholesterol/squalene solution with 500 µl of 10 mg/ml DHB solution (matrix). Three spots (0.5 µl) of this solution were also dispensed on to a metal target and allowed to air dry. Each spot on the metal target was analyzed in the MALDI-TOF-MS, and the peaks for both cholesterol (m/z 386) and squalene (m/z 410) and their metal adducts monitored.

Results

Demonstration that Contact Residues are Effectively Lifted from Latent Fingerprints The efficiency of the fingerprint lifting process and the ridge detail of the resultant prints were studied. Rhodamine 6G was used as a model contact agent due to its high fluorescence. Thus, prints of high fluorescence were seen following contact (upper and lower prints in FIG. 1A), whereas the normal print (centre of FIG. 1A) was not fluorescent under the scanning conditions used.

When the hydrophobic silica dusting agent was applied to the three prints, they became visually distinct (not shown) and all three prints now gave good clear prints on fluorescent scanning (FIG. 1B) due to the rhodamine fluorescence and also due to light scattered from the silica particles deposited on the print. Following lifting of the prints using lifting tape, little fluorescence remained on the surface of the glass slide (FIG. 1C), demonstrating the efficiency of the lifting process. Scans of the surface of the tape now revealed "fluorescent" prints demonstrating that the lifted prints and dusting agent remain intact during this process (FIG. 1D).

The results seen in FIGS. 1A-1D suggest that the application of commercial lifting tape results in transfer of the bulk of the deposited material of the latent fingerprint from the glass slide onto the tape. This would be the first step in the detection of any material on the latent fingerprint by MALDI-TOF-MS.

MALDI-TOF-MS Detection of Lifted Contact Residue (Rhodamine 6G)

Given the success of this experiment, it was hypothesized that the rhodamine lifted from the surface of glass microscope slides could be detected using MALDI-TOF-MS. The results are shown in the graph 200 illustrated in FIG. 2. The upper trace 205 is that from the lifted fingerprint and has a peak at m/z 443 corresponding to Rh 6G. The lower spectrum 210 is from the Rh 6G standard added directly to the MALDI target. The peak shapes and patterns are substantially similar suggesting the same compound. The decreased mass seen on the upper trace 205 is most likely due to the slight elevation of the tape used during deposition of the lifting tape onto the target plate, which would decrease the time of flight of the ionized species.

The conducting tape is designed to be stuck flat to a MALDI target and the sample added to the upper surface. It is also relatively fragile and is easily stretched, which could distort the original developed fingerprint. With some difficulty, it was used to lift the print from the microscope slide and was deposited on the MALDI target as best as possible. It was not possible to flatten it due to its fragility and tacky nature.

Figure 2:
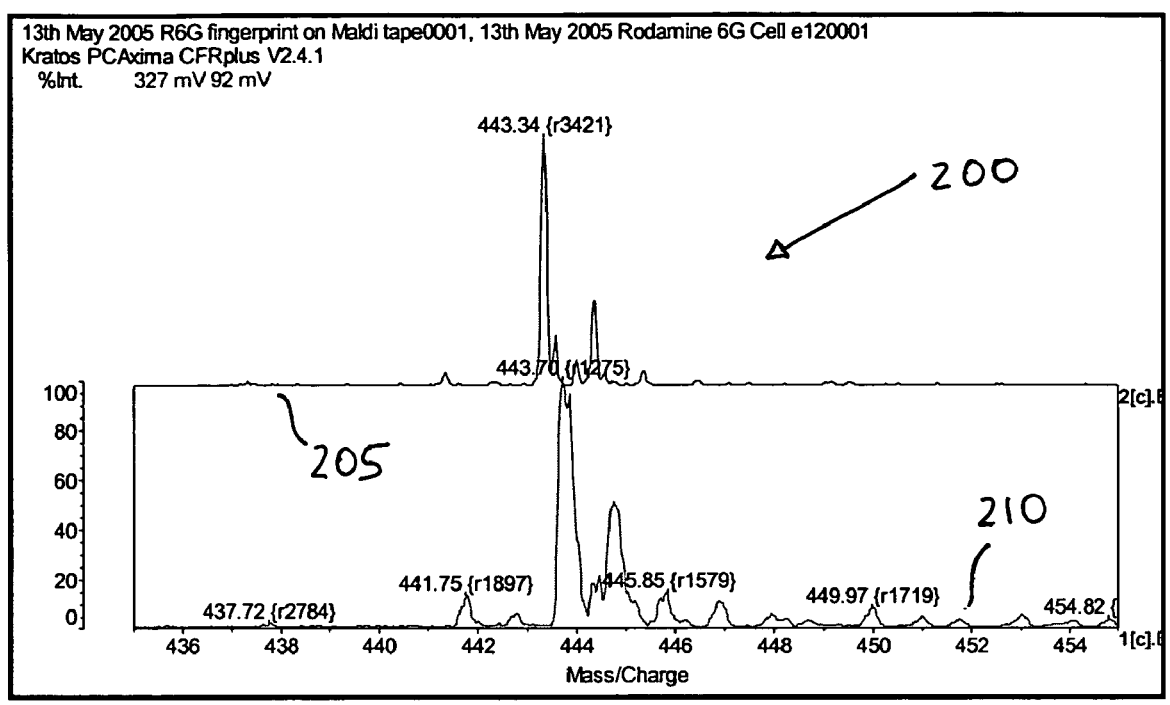
FIG. 2 is a graph illustrating the mass spectra of the rhodamine 6G deposited from ethanol (upper), and the rhodamine 6G from the lifted fingerprint (lower), both analyzed on MALDI tape, in accordance with an exemplary embodiment of the present invention.

The results shown in FIG. 2 demonstrate that contact residues, in the form of a powder, can be lifted from a surface and can be successfully detected using the MALDI-TOF-MS system.

Efficacy of Carbon Black Embedded Silica Particles as Enhancing Agents in the MALDI-TOF-MS for Cocaine To demonstrate that the results were being observed in the presence of both the matrix and the cocaine and were not from a background signal, further analyses were performed using known amounts of cocaine and matrix. The responses of magnetic silica particles in the presence and absence of cocaine were compared to responses of the blank target and cocaine without any matrix.

Figure 3:
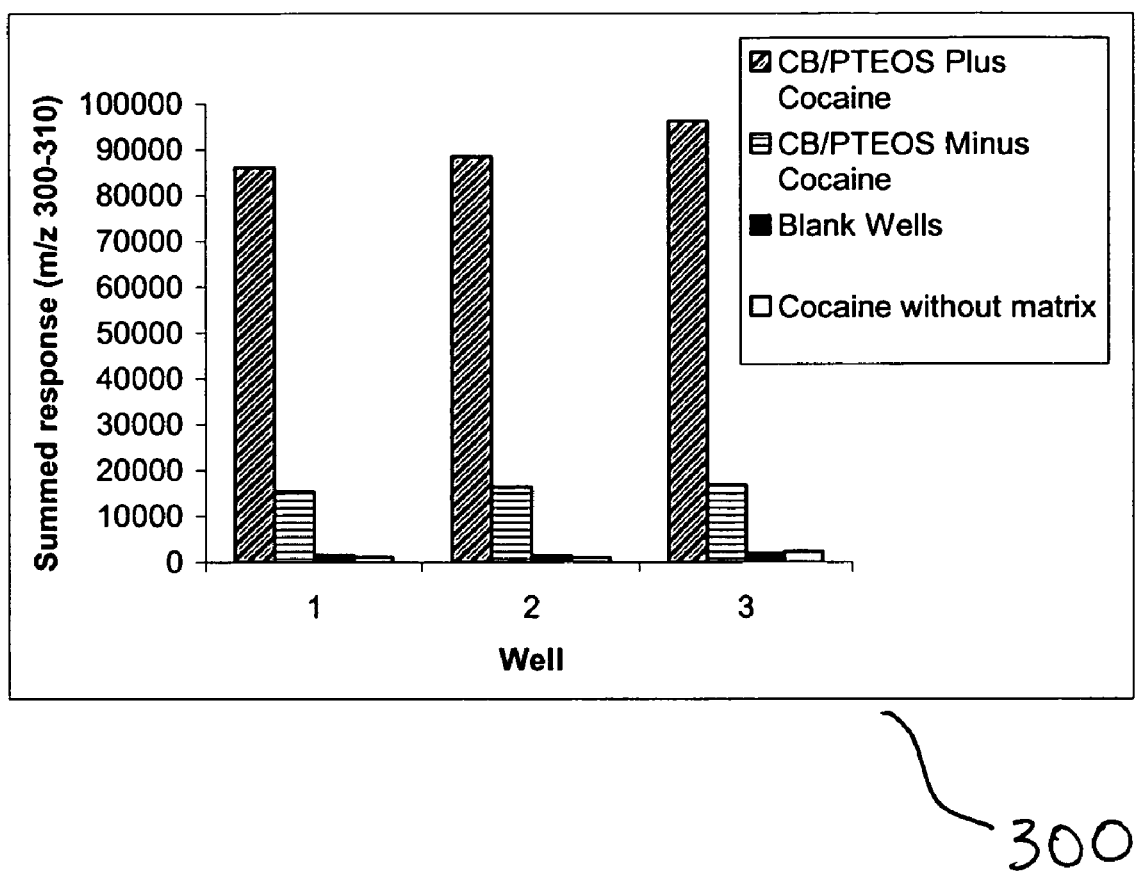
FIG. 3 is a graph illustrating the response of the MALDI-TOF-MS system to carbon black embedded silica particles in the presence and absence of cocaine hydrochloride, in accordance with an exemplary embodiment of the present invention.

The responses at m/z 304 of carbon black embedded silica particles in the presence and absence of cocaine were compared to responses of the blank target and cocaine without any DHB matrix. The intensities of the MS peaks due to cocaine are shown in graph 300 illustrated in FIG. 3. The presence of the silica particles resulted in a ten-fold increase in the peak intensity compared to that seen for cocaine in its absence. Good reproducibility was observed (mean intensity 90,275 and an rsd of 5.8%, n=3) compared with the corresponding results in the presence of DHB of 56,552 and an rsd of 112%, n=3.

Figure 4A:
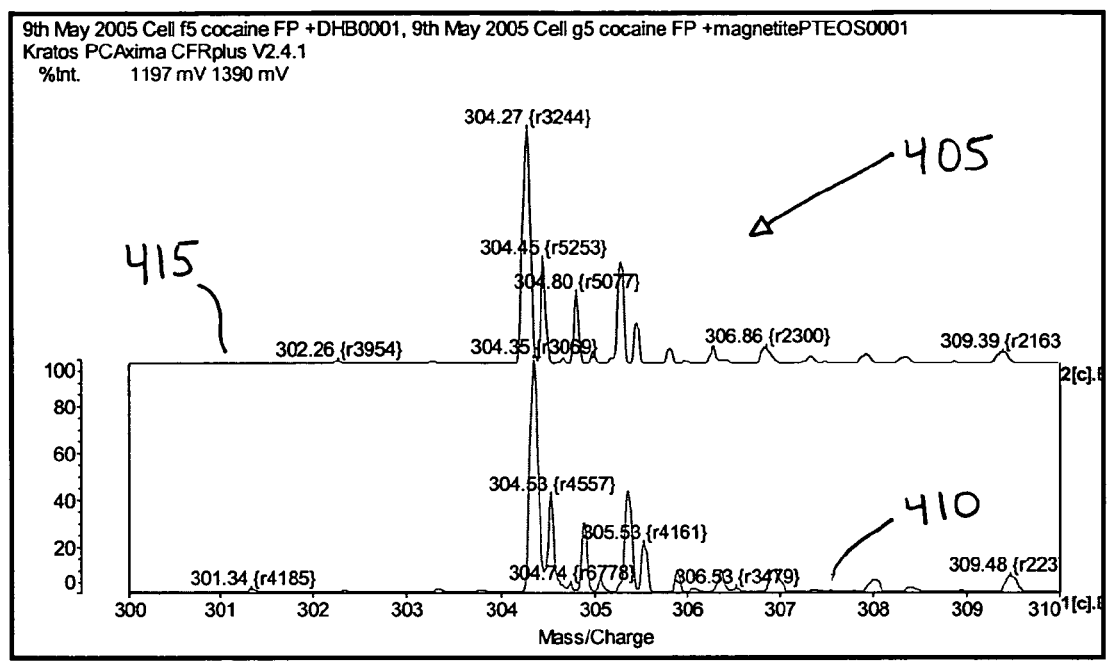

The potential SALDI use of carbon black embedded particles compared with conventional DHB matrix was studied. Cocaine hydrochloride was used as the target analyte, as the identification of this on fingerprints is of interest to the law enforcement agencies, since it could demonstrate that the individual providing the fingerprint had been in contact with cocaine. The mass spectra of cocaine in the presence of a conventional chemical matrix (DHB) and the new dusting matrix are shown in graph 405 illustrated in FIG. 4A for prints deposited directly onto the metal MALDI target. The lower spectrum 410 shows that of cocaine in the presence of DHB, while the upper spectrum 415 shows cocaine in the presence of magnetic PTEOS nanoparticles, deposited by the magnetic wand. Both show similar spectra, corresponding to that of the drug, but with an apparently increased response in the presence of the magnetic particles. This shows that magnetic PTEOS particles assist with the desorption process of cocaine in a similar manner to that of the conventional matrix. The magnetic PTEOS also showed potential as a fingerprint visualization powder as good ridge detail was observed on the developed prints (not shown).

Figure 4B:
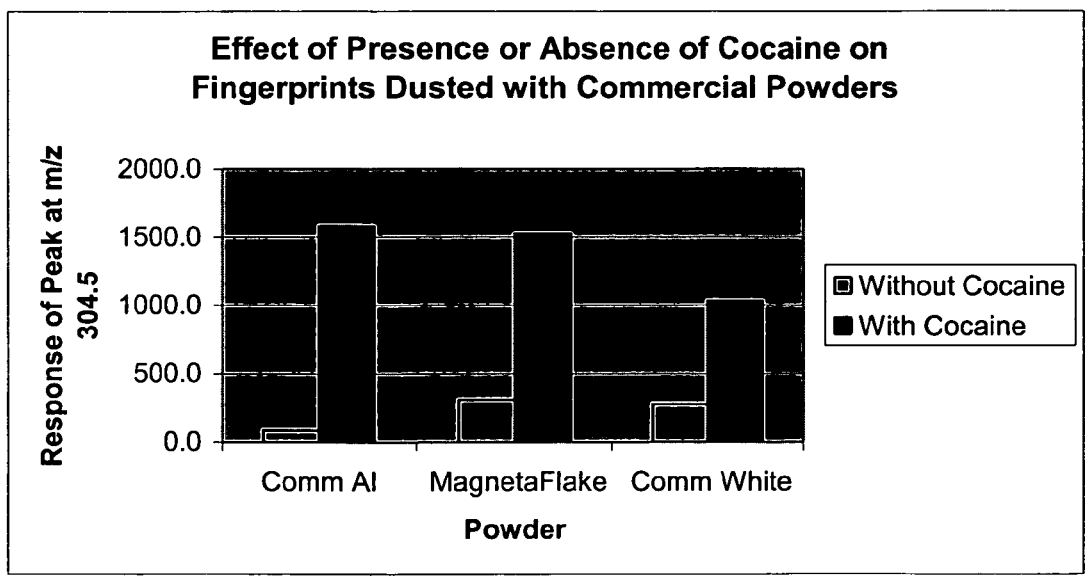

Similar results were also observed for cocaine peaks at 304.5 m/z for contact prints deposited onto a metal target plate and dusted with hydrophobic powders containing titanium dioxide, carbon black (1:10), or treated with DHB or left untreated (details not shown) when the relative intensities were 1,700, 10,000, 9,000 and 100 mV respectively (shown in graph 420 illustrated in FIG. 4B).

Figure 5:
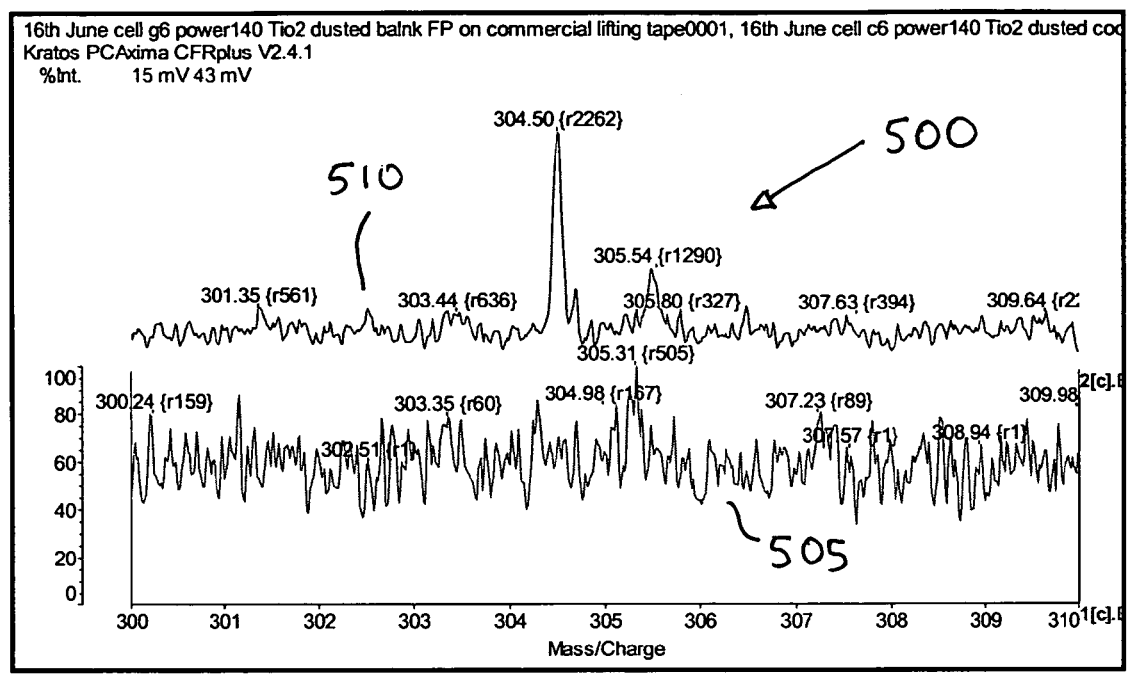
FIG. 5 is a graph that: illustrates the mass spectra of lifted latent fingerprints dusted with $TiO_2$-embedded hydrophobic silica particles to detect contact with cocaine; positive contact (upper trace), and no contact with cocaine (lower trace) in accordance with an exemplary embodiment of the present invention.
Figure 6:
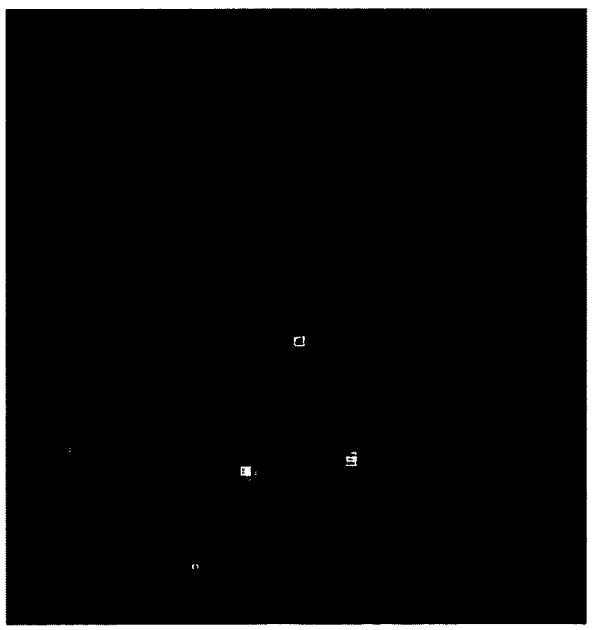
FIG. 6 is a photograph of a single well/cell unit on the surface of a 96-well MALDI-target plate located within the mass spectrometer, showing the ridge detail (light stripes) of a lifted fingerprint pre-dusted with $TiO_2$-embedded hydrophobic silica particles, prior to analysis by MALDI-TOF-MS, in accordance with an exemplary embodiment of the present invention.

Effectiveness of $TiO_2$-Embedded Particles for the Detection of Cocaine Residues on Lifted Fingerprints Having demonstrated the efficacy of the lifting process (see FIGS. 1 and 2), and the detection of cocaine from spiked latent prints on the MALDI targets (see FIGS. 3-4), it was hypothesized that cocaine could be detected on lifted fingerprints directly off the commercial lifting tape. The results are shown in the graph 500 illustrated in FIG. 5. The lower trace 505 is that observed for the lifted print that has not been in contact with cocaine, while the upper trace 510 is from a print that was in contact with the drug. A clear peak is only seen in the upper trace 510 at m/z at 304 corresponding to cocaine. In both cases, the original prints were dusted with $TiO_2$-embedded hydrophobic silica particles. FIG. 6 shows the target area analyzed by the MALDI-TOF of the fingerprint spiked with cocaine. A similar picture was obtained for the negative control (not shown). The well diameter is 3.4 mm and the clear ridge detail of the fingerprint can be observed. The spectra in FIG. 5 were obtained by laser scanning over the areas defined within the cells and the signals averaged to produce the spectra.

Detection of Cholesterol and Squalene from Fingerprints by Use of MALDI-TOF-MS, Using the Hydrophobic Particles as Enhancing Matrix In this experiment, 12 prints were deposited directly onto a stainless steel MS target plate. After aging, the prints were dusted with one of ten different formulations of hydrophobic dusting agent. The prints were then lifted and interrogated using the MALDI-TOF-MS system.

Figure 7:
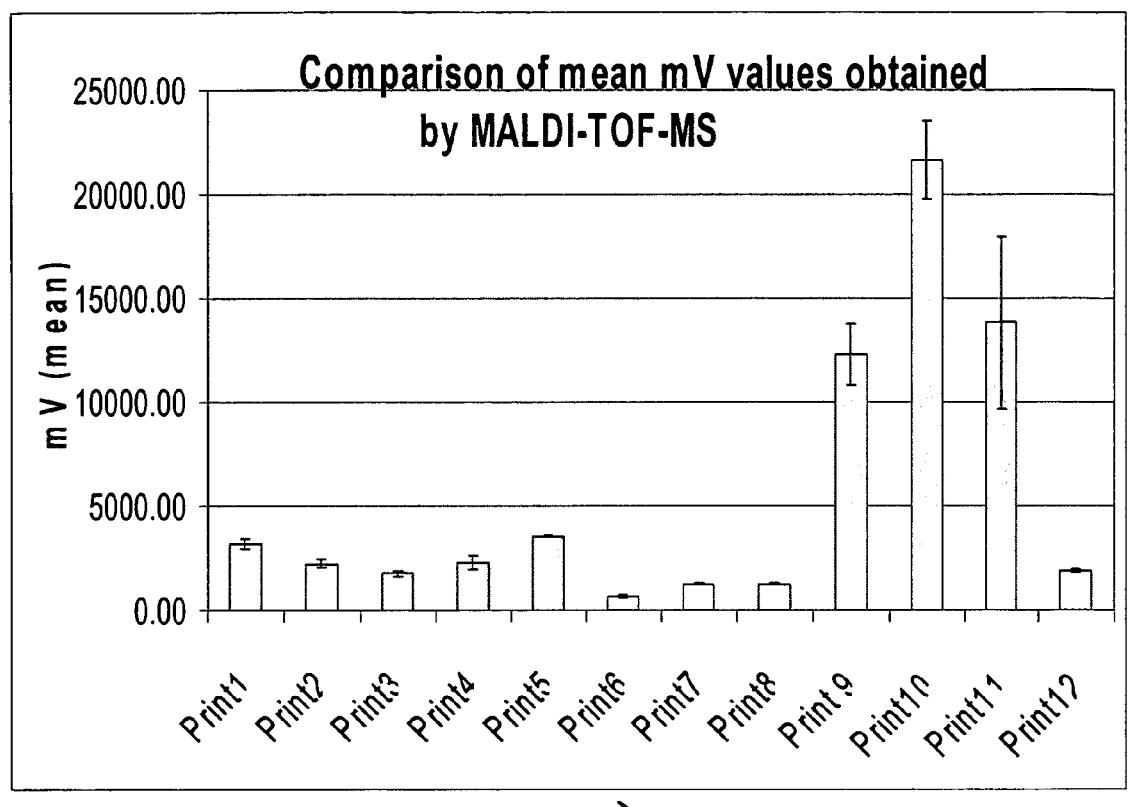
FIG. 7 is a graph illustrating relative intensities at m/z 433.55 (molecular ion for squalene plus sodium adduct) for lifted prints dusted with 10 formulations of hydrophobic particles (1-10) and controls (11 and 12), in which no peaks at m/z 386 due to cholesterol were observed, in accordance with an exemplary embodiment of the present invention.

It was assumed that both cholesterol and squalene would be detected, but in practice only squalene was observed. This was seen at m/z of 433 corresponding to the molecular ion plus the sodium adduct. As shown in the graph 700 illustrated in FIG. 7, the intensity observed in the absence of any enhancing agent was about 2,000 mV (print 12). This was enhanced to about 14,000 by DHB. Of the powders, those containing the highest proportions of carbon black gave the best responses (prints 9 and 10), and the higher proportion of carbon the more intense the peak, so that the sample with the greatest intensity of about 22,000 mV was associated with a carbon black: dilution ratio of 1:2.

Generally, the presence of DHB within the powder slightly enhanced the peak intensity (prints 1 and 2-titanium dioxide, and prints 4 and 5-carbon black, ratio of 1:10), but this trend was not seen for powders containing the dyes crystal violet (prints 3 and 6) and rhodamine 6G (prints 7 and 8) where low signals equivalent to or less than the untreated print 12 were produced.

Direct Detection of Cholesterol and Squalene by Use of MALDI-TOF-MS, Using the Hydrophobic Particles as Enhancing Matrices Since cholesterol was not seen in the MS of the prints, it was decided to determine whether this compound could be detected using the MALDI-TOF-MS system in the presence of DHB and the new dusting agents. Hence, standards of a mixture of squalene and cholesterol were deposited onto the surface of a metal target plate and eight sets of these spots in triplicate were dusted with the eight formulations of hydrophobic powders used above, or were treated with DHB, or were left untreated.

Figure 8:
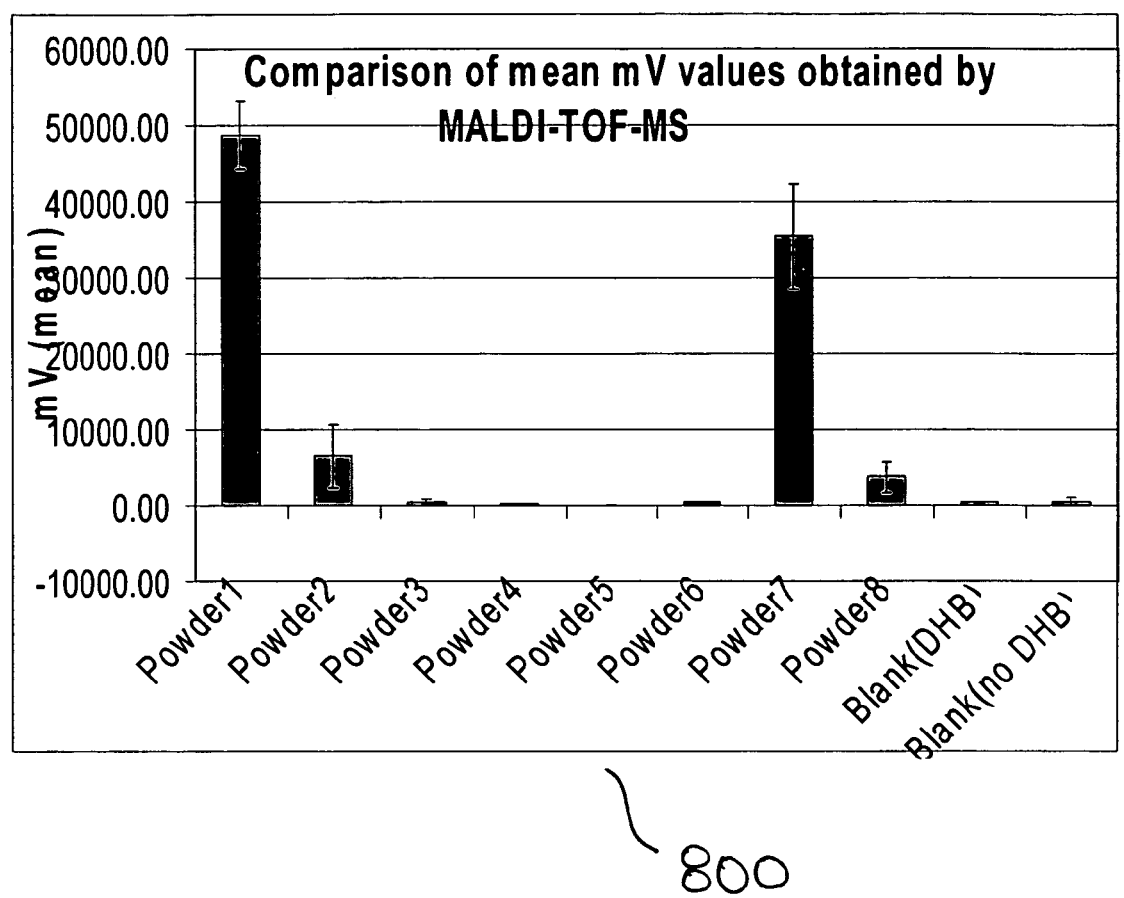
FIG. 8 is a graph illustrating relative intensities at m/z 433.55 (squalene, formula weight 410.72, plus sodium (22.99) adduct) for squalene standards in the presence of eight formulations of hydrophobic powders (1-8) and two controls (9, 10), in accordance with an exemplary embodiment of the present invention.

In this case, peaks due to squalene were again observed at m/z of 433 due to the sodium adduct of the compound, with powders 1, 2, 7 and 8 giving signals that were appreciably greater than the intensity seen in the presence of DHB (shown in graph 800 illustrated in FIG. 8). The greatest intensity was seen with red fluorescent powder (rhodamine 6G, powder 1, 49,000 mV), with carbon black again giving good responses (1:10, 6000 mV; 1:5, 36,000 mV; and 1:2, 4,000 mV).

Figure 9:
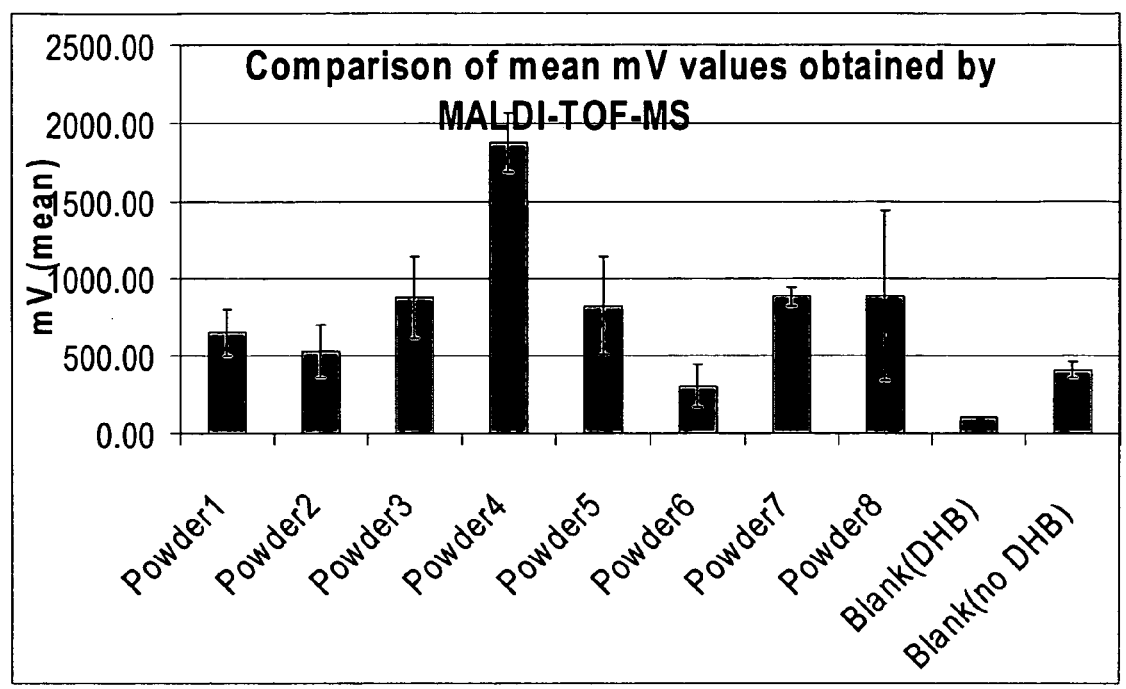
FIG. 9 is a graph illustrating relative intensities at m/z 386.37 (formula weight 386.65 for cholesterol) for cholesterol standards in the presence of eight formulations of hydrophobic powders (1-8) and two controls (9, 10), in accordance with an exemplary embodiment of the present invention.

A peak at m/z of 386 was now observed, but in all cases the intensity values were much lower than those seen for squalene. As shown in graph 900 illustrated in FIG. 9, the highest was produced in the presence of powder containing crystal violet dye (1,800 mV, powder 4), with those containing carbon black also producing relatively good peaks (all about 800 mV for powder 3, 1:10 plus DHB, powder 7, 1:5 and powder 8, 1:2).

The actual spectra 1005 and 1010 for these two compounds are shown in FIG. 10A (squalene) and FIG. 10B (cholesterol), respectively. These spectra 1005 and 1010 clearly show the better response of squalene under the conditions used.

Direct Detection of Exogenous Metabolites from Smokers in Dusted Latent Fingerprints Using MALDI-TOF-MS The hydrophobic dusting agent used was a carbon black incorporated agent formed with a starting ratio of carbon black:PTEOS of 1:2, the synthesis of which is described in the next section of this specification.

The dusting agent was homogeneously incorporated into a mixture of fine iron particles (diameter <60 μM) and stearic acid (1.0% w/w), such that the ratio of hydrophobic particles to iron particles was 2:98 w/w. Latent prints were dusted using a commercial magnetic wand and either analyzed in situ for prints on the surface of stainless steel plates (e.g., Shimadzu MALDI-TOF-MS target plates), or lifted using commercial lifting tape. The lifted prints were attached, print side up, on the target plates using commercial adhesive tape. MALDI-TOF-MS was performed using a Kratos Axima CFR Plus MALDI-TOF-MS (Shimadzu Biotech, Manchester, UK), operated in positive ion reflectron mode. The commercial matrix used was 2,5-dihydroxybenzoic acid (DHB) (10 mg ml$^{-1}$ in 50:50 acetonitrile: deionised water [dH$_2$O]).

Figure 11:
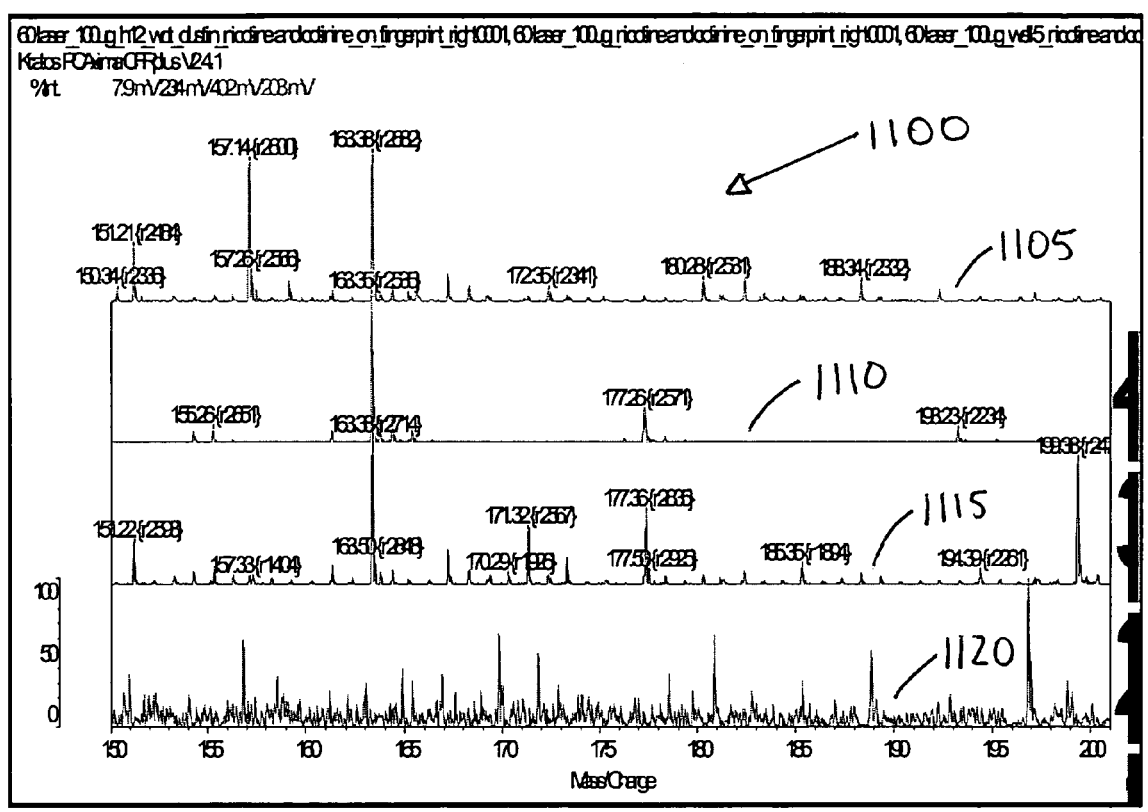
FIG. 11 is a graph illustrating: MALDI-TOF-MS of latent fingerprints from a non-smoker (FR) on a stainless steel plate and spiked with 10 μl of a solution containing a 1 μg/ml mixture of nicotine (RMM 163) and cotinine (RRM 176), in accordance with an exemplary embodiment of the present invention

The results shown in graph 1100 illustrated in FIG. 11 demonstrate that no peak due to nicotine (FW 162) or cotinine (FM 176) is observed in the absence of a matrix enhancing agent for a latent print that is spiked with the mixture of nicotine and cotinine (10 ng of each, spectrum 1120). When the conventional matrix assisting agent DHB is added to prints that have been spiked with of each compound, then peaks at 163 and 177 are observed (spectrum 1110). When the hydrophobic dusting agent is added to the spiked latent prints then peaks at 163 and 177 are again observed indicating that this agent also acts as an enhancing agent. An additional peak at m/z 199 is now observed probably due to the sodium adduct of cotinine. A peak at m/z 157 is observed in the spectrum for an unspiked print dusted with the hydrophobic dusting agent, together with a peak at m/z at 163, of approximately the same intensity. No peaks at 177 and 199 are seen in this spectrum (spectrum 1105). It should be noted that in spectrum 1115, the peak at 163 is of considerably greater intensity than the peak at 157 presumably due to the presence of nicotine.

FIG. 11 clearly demonstrates that nicotine and cotinine (both 10 ng per print) when applied to latent fingerprints cannot be detected by TOF-MS only when no matrix enhancer such as DHB is added (spectrum 1120 compared with spectrum 1110). FIG. 11 also demonstrates that the hydrophobic dusting agent used to develop the latent print also acts as an enhancer so that these compounds are again detected (spectrum 1115). Major peaks were found at m/z values of 163.3 (formula weight for nicotine is 162.23) and 177.3 (formula weight for cotinine is 176.22) and 199.2. This last peak is possibly due to the sodium adduct of cotinine (C$_{10}$H$_{12}$N$_2$ONa, formula weight 199.21). These peaks are absent from the pre-dusted latent fingerprint that was not spiked with nicotine and cotinine (1105).

Figure 12A:
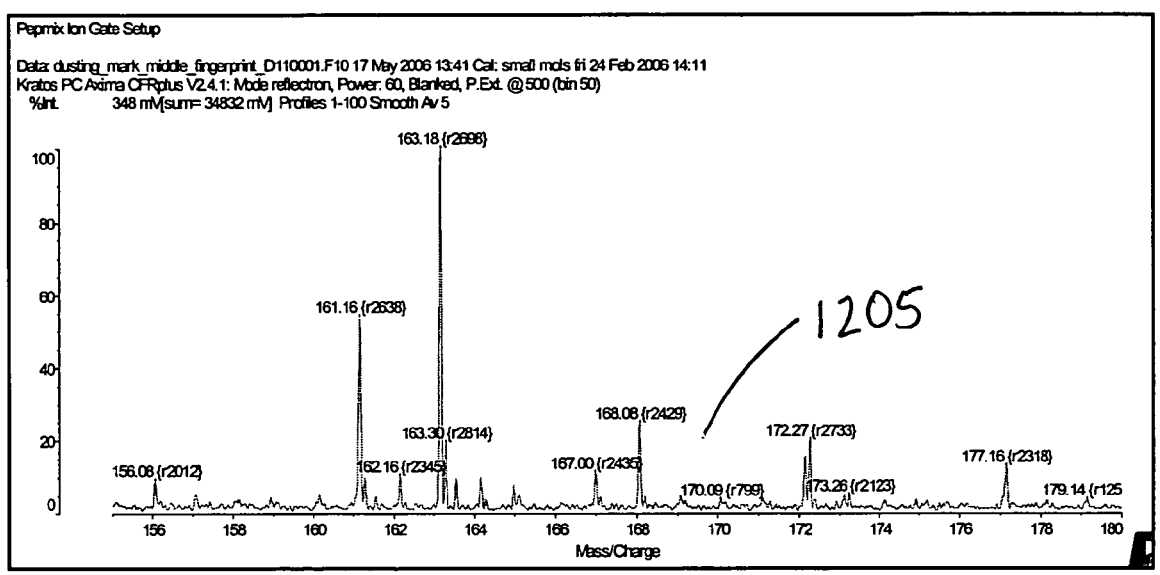
FIGS. 12A-12C are graphs illustrating MALDI-TOF-MS of latent fingerprints from an ex-smoker (24 hours since last cigarette) deposited on a stainless steel pre-dusted with hydrophobic particles, wherein FIG. 12A comprises m/z range 155-180, FIG. 12B comprises m/z range 180-205, and FIG. 12C comprises m/z range 205-450, in accordance with an exemplary embodiment of the present invention.
Figure 12:
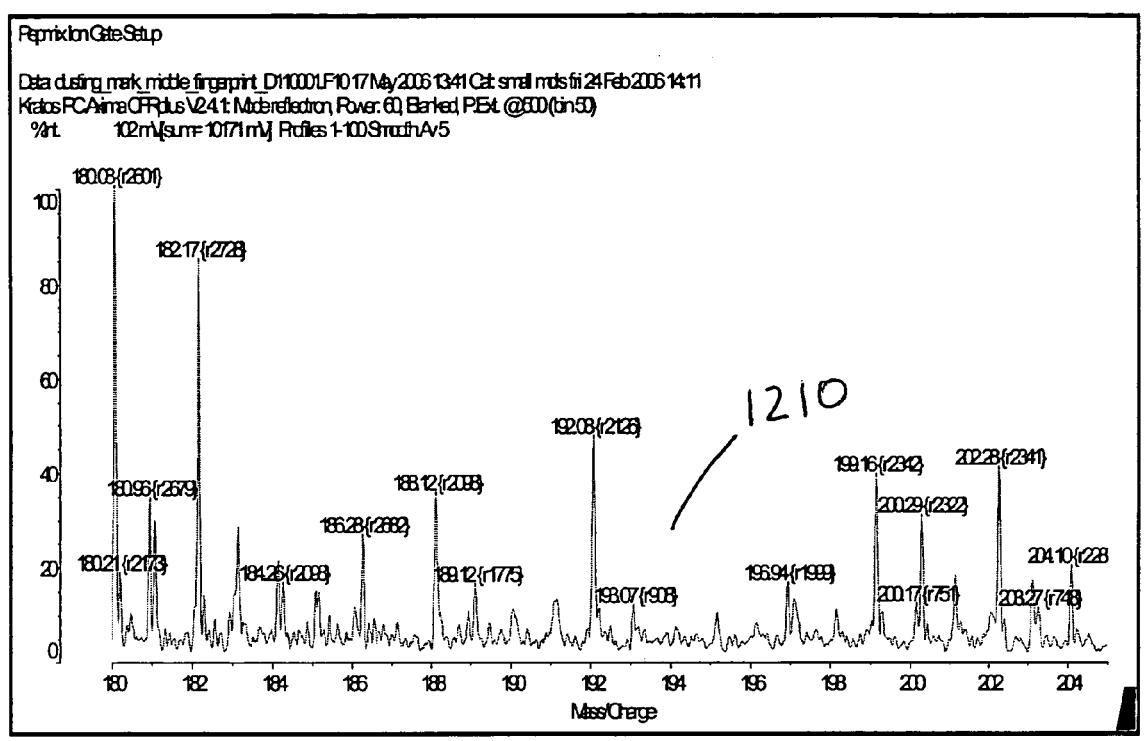
Figure 12C:
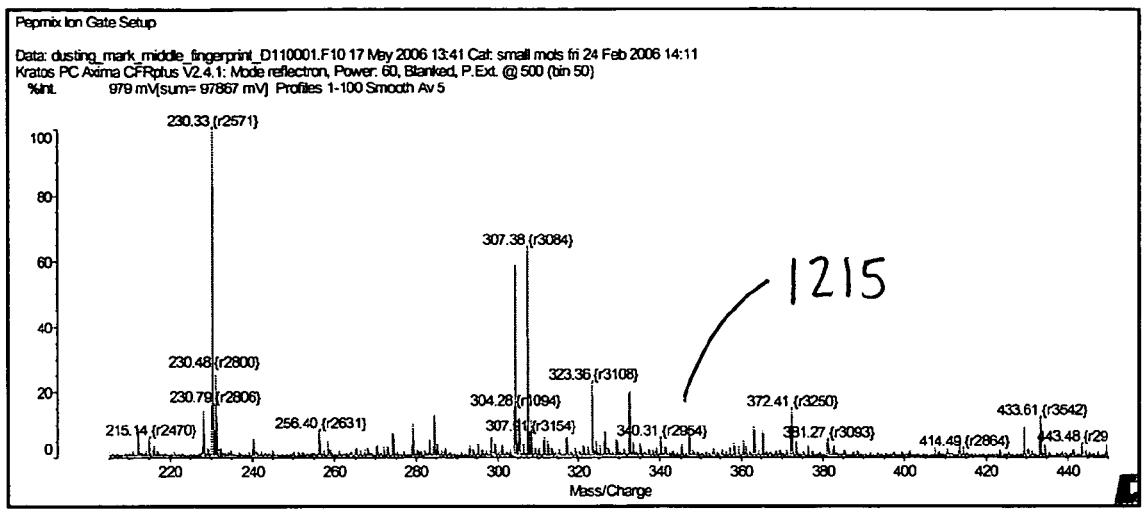
Figure 13:
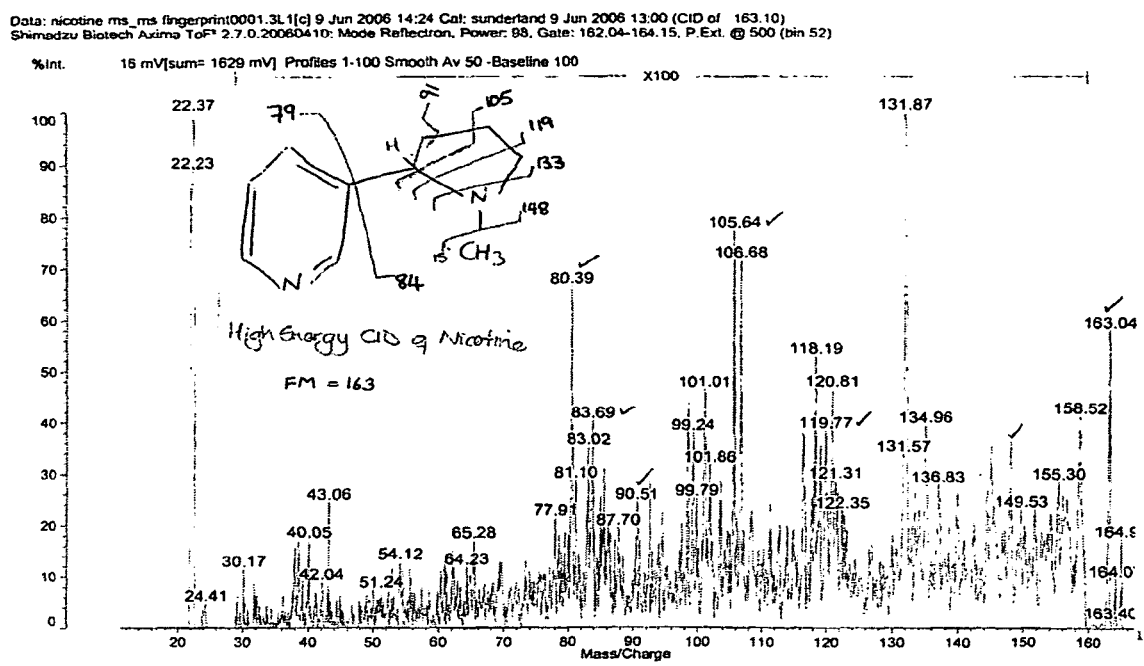
FIG. 13 is a graph illustrating MALDI-TOF-MS-MS of latent fingerprints from a dusted print of a smoker, wherein peaks at 163, 148, 133, 119, 105, 91, 84 and 79 are characteristic of nicotine and give unambiguous proof of its presence, in accordance with an exemplary embodiment of the present invention.
Figure 14:
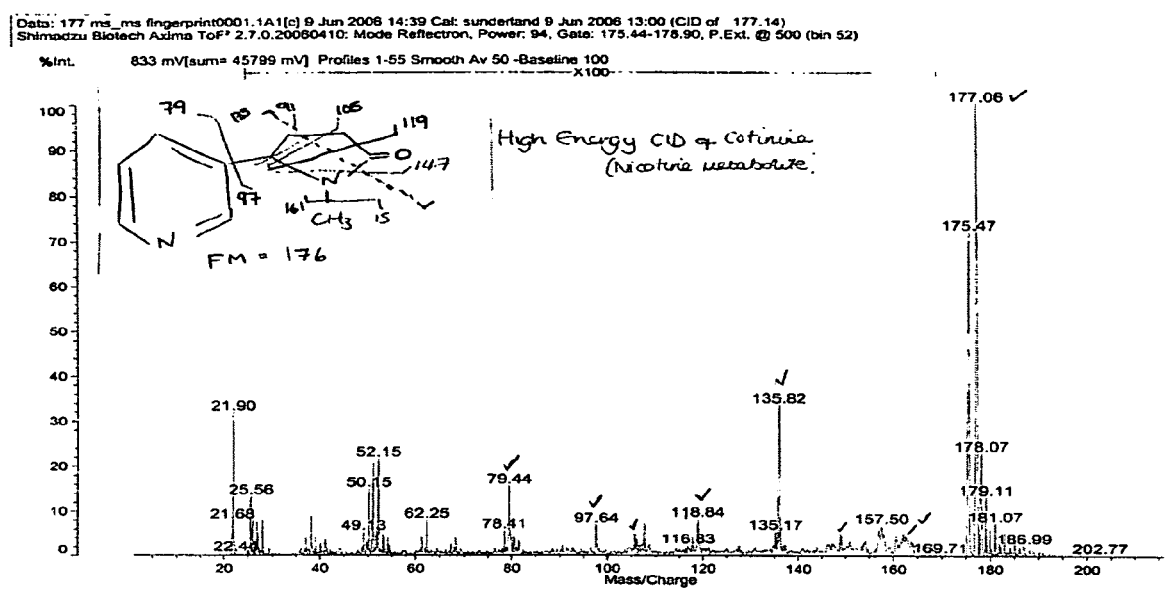
FIG. 14 is a graph illustrating MALDI-TOF-MS-MS of latent fingerprints from a dusted print of a smoker, wherein peaks at 177, 161, 147, 135, 119, 105, 97, 91 and 79 are characteristic of cotinine and give unambiguous proof of its presence, in accordance with an exemplary embodiment of the present invention.

The corresponding spectra 1205, 1210 and 1215 for an ex-smoker who had not smoked for 24 hours are shown in FIGS. 12A-12C. Major peaks not due to the dusting matrix are seen at m/z of 163.1 (nicotine) and 199.1 (cotinine sodium adduct) with a minor peak at 177.1 (cotinine).

It is of interest to note that when the spectra at higher mass numbers are examined, peaks at 307.4 and 433.4 (FIG. 12C) are seen for prints applied directly to the stainless steel plates. These are probably due to the sodium adduct of stearic acid (FW 307.47) and the sodium adduct of squalene (FW 433.71), respectively. These originate from the stearic acid used in the formulation of the dusting agent, and from natural squalene secreted as an endogenous component of the fingerprint.

These peaks can be used to calibrate the peaks obtained with lifted prints, since they are present on the surface of the lifting tape that is itself attached to the surface of the stainless steel target plate. This raises the surface so the time of flight of the ionized species is now less than from the steel surface and the apparent m/z values of the peaks are less. Thus, for spectra obtained for the prints from smokers on lifted tapes, the peaks for the sodium adducts are seen at 305.1 and 431.2, together with peaks at 174.6 (major) and 197.4. The lower masses of the peaks can be corrected by 2.3 m/z units giving peaks at 176.9 (cotinine) and 199.7 (sodium cotinine adduct).

The peaks at 161, 167 and 168 are consistently seen only in the MS of smokers. It is known that although nicotine constitutes about 95% of the alkaloids in tobacco leaves, a variety of other alkaloids are also present. Of these, nornicotine (RMM 148) and anatabine (RMM 160) are the most abundant, as discussed in, for example, the Hukkanen reference. The peak at m/z at 161 could be the due to anatabine, since the protonated forms of nicotine and cotinine are observed in the spectra.

Preparation of Carbon Black Incorporated Agent

A method for the preparation of blank nanoparticles involves mixing 30 ml ethanol, 5 ml dH$_2$O, 2.5 ml of tetraethoxysilane (TEOS) and 2.5 ml phenyltriethoxysilane (PTEOS) in a centrifuge tube. To this mixture, add 2 ml ammonium hydroxide solution and rotate the solution overnight. After this time, centrifuge the suspension (about 3 minutes at 3,000 RPM).

The product is isolated following a series of centrifugation and washing steps using 10:90 v/v ethanol/water and then retained as a suspension in 97:3 v/v water/ethanol. These were also subjected to particle size distribution analysis and SEM and TEM.

For carbon black particles, 5 ml of a 1:100 fold dilution of carbon black solution in water is added to the precursor solution. For TEOS:PTEOS coated magnetic particles, particulate magnetite is prepared according to methods known to those of ordinary skill and 5 ml of the suspension in water added to the precursor solution.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, exemplary embodiment or example of the present invention are to be understood to be applicable to any other aspect, exemplary embodiment or example described herein unless incompatible therewith.

Throughout this disclosure, various aspects of this present invention can be presented in a range format. It should be understood that the description in range format is merely for convenience and brevity and should not be construed as an inflexible limitation on the scope of the present invention. Accordingly, the description of a range should be considered to have specifically disclosed all the possible sub-ranges as well as individual numerical values within that range. For example, description of a range, such as from 1 to 6, should be considered to have specifically disclosed sub-ranges, such as from 1 to 3, from 1 to 4, from 1 to 5, from 2 to 4, from 2 to 6, from 3 to 6 and the like, as well as individual numbers within that range, for example, 1, 2, 3, 4, 5, and 6. This applies regardless of the breadth of the range. It should also be understood that description of a number of ranges should be considered to have specifically disclosed a combination of end points.

It will be appreciated by those of ordinary skill in the art that the present invention can be embodied in various specific forms without departing from the spirit or essential characteristics thereof. The presently disclosed embodiments are considered in all respects to be illustrative and not restrictive. The scope of the present invention is indicated by the appended claims, rather than the foregoing description, and all changes that come within the meaning and range of equivalence thereof are intended to be embraced.

All U.S. patents and applications, foreign patents and applications, and publications discussed above are hereby incorporated by reference herein in their entireties.

What is claimed is:

1. A method of determining the presence of a residue within a fingerprint, comprising the step of:
   (a) using a matrix-assisted mass spectrometry technique to determine the presence of the residue within the fingerprint.
2. The method of claim 1, wherein the matrix-assisted mass spectrometry technique comprises one of MALDI-TOF-MS and SALDI-TOF-MS.
3. The method of claim 1, wherein the matrix-assisted mass spectrometry technique comprises at least one of MALDI-TOF-MS-MS and SALDI-TOF-MS-MS.
4. The method of claim 1, wherein the residue comprises an endogenous residue.
5. The method of claim 4, wherein the endogenous residue comprises at least one of an endogenous metabolite and an exogenous metabolite.
6. The method of claim 5, wherein the endogenous metabolite comprises squalene.
7. The method of claim 5, wherein the exogenous metabolite comprises a metabolite of nicotine.
8. The method of claim 7, wherein the metabolite of nicotine comprises cotiine.
9. The method of claim 1, wherein the residue comprises a contact residue.
10. The method of claim 9, wherein the contact residue comprises a narcotic.
11. The method of claim 10, wherein the narcotic comprises cocaine.
12. The method of claim 1, wherein at least one endogenous residue and at least one contact residue are co-deposited within the fingerprint.
13. The method of claim 1, comprising the steps of:
    (b) applying particulate matter to the fingerprint that is configured to (i) act as a matrix in the matrix-assisted mass spectrometry technique and (ii) aid at least one of detection and imaging of the fingerprint, to form a particulate-applied fingerprint; and
    (c) subjecting material forming the particulate-applied fingerprint to mass spectrometry to detect one of the presence and absence of the residue.
14. The method of claim 13, wherein the particulate matter is hydrophobic.
15. The method of claim 13, wherein the particulate matter comprises hydrophobic silica particles.
16. The method of claim 13, wherein the particulate matter comprises one of a metal, metal nitride, metal oxide and carbon.
17. The method of claim 16, wherein the metal oxide comprises one of titanium oxide, iron oxide (magnetite), haematite and combinations thereof.
18. The method of claim 16, wherein the carbon comprises one of carbon black, a fullerene compound, carbon nanotubes, graphite, an analog thereof or combinations thereof.
19. The method of claim 16, wherein the metal comprises one of aluminum, iron and combinations thereof.
20. The method of claim 13, wherein the particulate matter comprises hydrophobic silica particles, and
    wherein one of metal, metal nitride, metal oxide and carbon particle is embedded within the hydrophobic silica particles.
21. The method of claim 20, wherein an average diameter of the hydrophobic silica particles comprises one of less than and equal to about 100 μm.
22. The method of claim 20, wherein the average diameter of the hydrophobic silica particles comprises one of less than and equal to about 1 μm.
23. The method of claim 13, wherein the particulate material comprises a dye molecule.
24. The method of claim 23, wherein the dye molecule comprises one of fluorescent or colored.
25. The method of claim 23, wherein the dye molecule is embedded within a hydrophobic silica particle.
26. The method of claim 23, wherein the particulate matter is one of magnetic or paramagnetic.
27. The method of claim 13, wherein the fingerprint is lifted from a site of deposition of the fingerprint using a lifting tape and contacted with a mass spectrometry sample support, after the particulate matter is applied to the fingerprint.
28. The method of claim 1, wherein the fingerprint is a partial print of a body part.
29. A method of determining the presence of a residue within a fingerprint, comprising the step of:
    (a) using a matrix-assisted mass spectrometry technique to determine the presence of the residue within the fingerprint,
    wherein the matrix-assisted mass spectrometry technique comprises one of MALDI-TOF-MS and SALDI-TOF-MS;
    (b) forming a particulate-applied fingerprint by applying particulate matter to the fingerprint that is configured to (i) act as a matrix in the matrix-assisted mass spectrometry technique and (ii) aid at least one of detection and imaging of the fingerprint; and
    (c) subjecting material forming the particulate-applied fingerprint to mass spectrometry to detect one of the presence and absence of the residue.
30. The method of claim 29, wherein the fingerprint is a partial print of a body part.
31. A method of fingerprint analysis, comprising the step of:
    a.) determining presence of a residue within a fingerprint by using a matrix-assisted mass spectrometry technique, wherein the matrix-assisted mass spectrometry technique comprises one of MALDI-TOF-MS and SALDI-TOF-MS.
32. The method of claim 31, wherein the fingerprint is a partial print of a body part.

* * * * *